(12) United States Patent
Neilan et al.

(10) Patent No.: US 8,057,505 B2
(45) Date of Patent: Nov. 15, 2011

(54) EMBOLIC PROTECTION DEVICE

(75) Inventors: John Neilan, Gort (IE); Ronan Keating, Knocknacarra (IE); David Vale, Clontarf (IE)

(73) Assignee: Salviac Limited, Dublin (IE)

( * ) Notice: Subject to any disclaimer, the term of this patent is extended or adjusted under 35 U.S.C. 154(b) by 1361 days.

(21) Appl. No.: 11/406,822

(22) Filed: Apr. 18, 2006

(65) Prior Publication Data

US 2006/0293705 A1  Dec. 28, 2006

Related U.S. Application Data

(60) Provisional application No. 60/672,432, filed on Apr. 18, 2005.

(51) Int. Cl.
*A61M 29/00* (2006.01)
*A61F 2/06* (2006.01)

(52) U.S. Cl. ...................................... 606/200; 623/1.11

(58) Field of Classification Search ................... 606/200; 623/1.11
See application file for complete search history.

(56) References Cited

U.S. PATENT DOCUMENTS

| 6,918,921 B2 * | 7/2005 | Brady et al. ................... 606/200 |
| 2004/0172055 A1 | 9/2004 | Huter et al. |

FOREIGN PATENT DOCUMENTS

| WO | WO 03/055412 A2 | 7/2003 |
| WO | WO 2004/030574 A1 | 4/2004 |
| WO | WO 2004/041125 A1 | 5/2004 |

* cited by examiner

*Primary Examiner* — Vy Q Bui
(74) *Attorney, Agent, or Firm* — Sughrue Mion, PLLC; Jonathan D. Feuchtwang

(57) ABSTRACT

An embolic protection device (2000) comprises a collapsible filter body (102), a filter support (103) for supporting the filter body (102), and a tubular member (108) to which the filter support (103) is mounted. The filter support (103) comprises two round wires (116). Each wire (116) has a "M"-shaped curve (120) in the wire (116) which acts as a strain distributing linking element. In an extended configuration, the concave portion of each curve (120) faces longitudinally in the distal direction. In a collapsed configuration, the concave portion faces radially inwardly towards the tubular member (108) and wraps around part of the tubular member (108) to define a compact, low-profile filter support (103). Tethers (500, 501) extend between the curves (120) and a sleeve (201) slidably mounted to the tubular member (108). The distal end of each tether (500, 501) is fixedly attached to the sleeve (201) and to the filter body (102). The sleeve (201) is slidable over the tubular member (108) between a pair of stops.

40 Claims, 31 Drawing Sheets

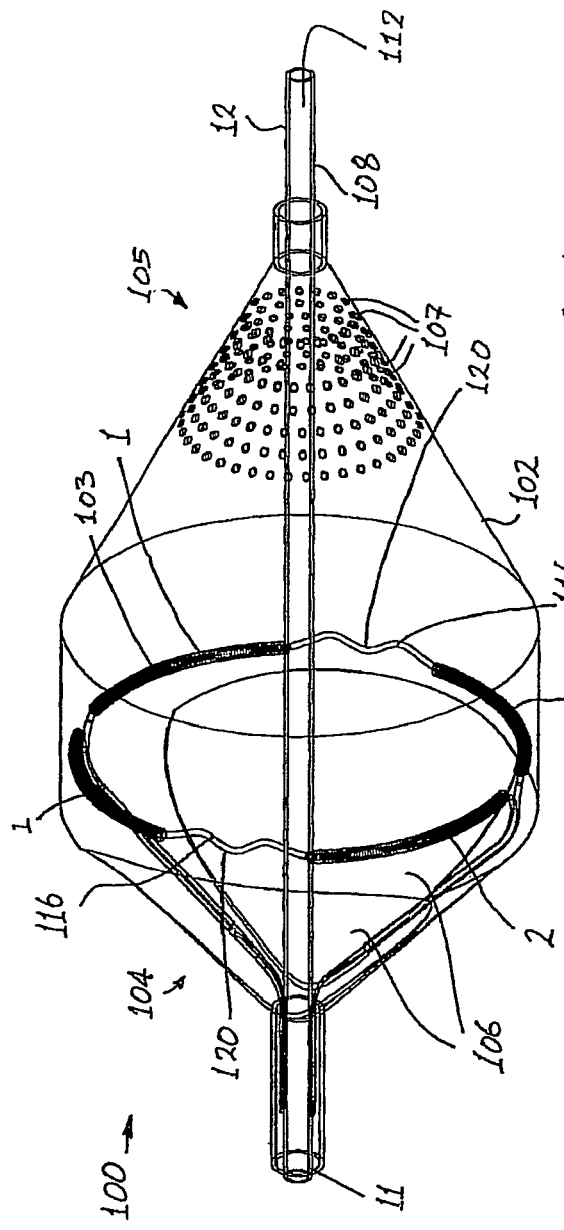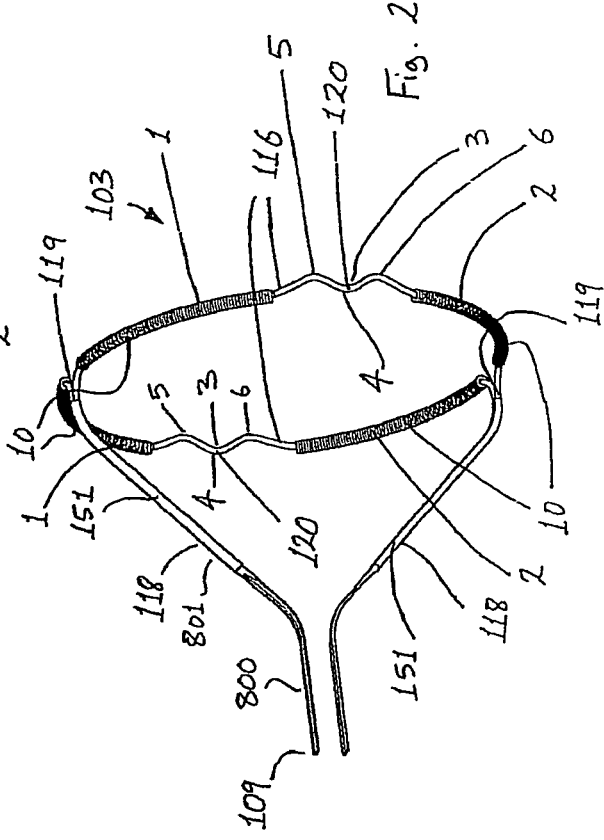
Fig. 1
Fig. 2

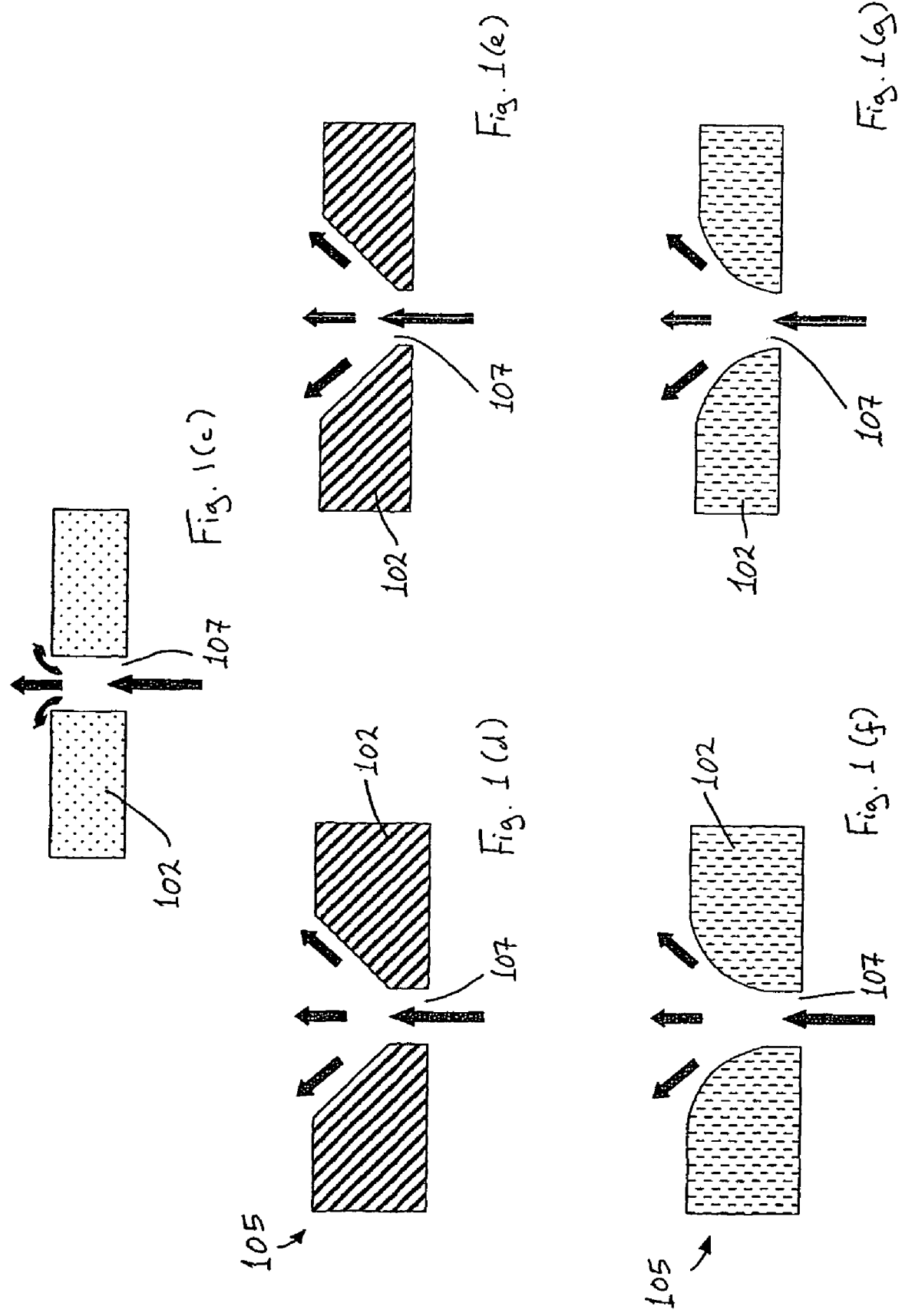

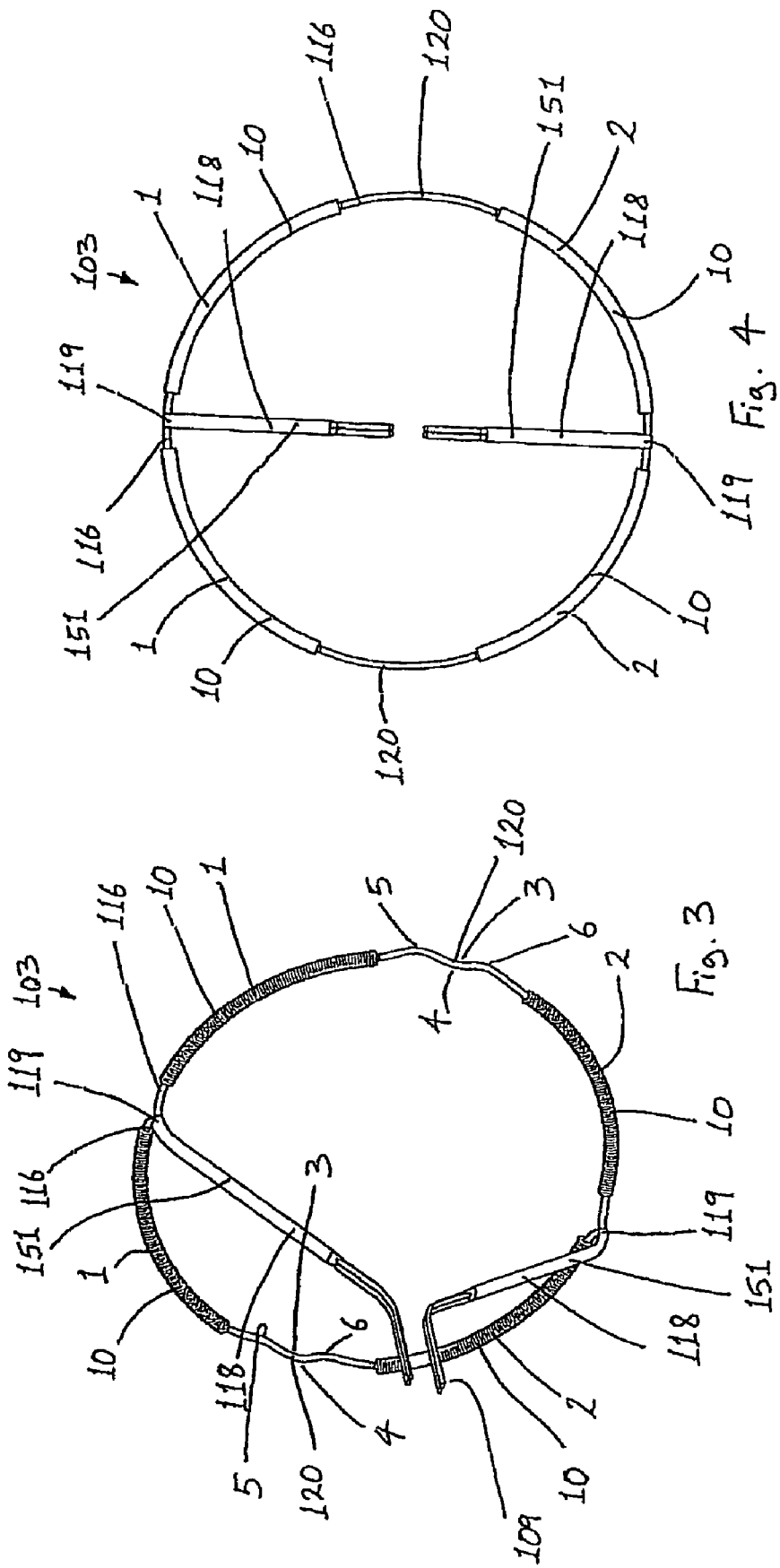

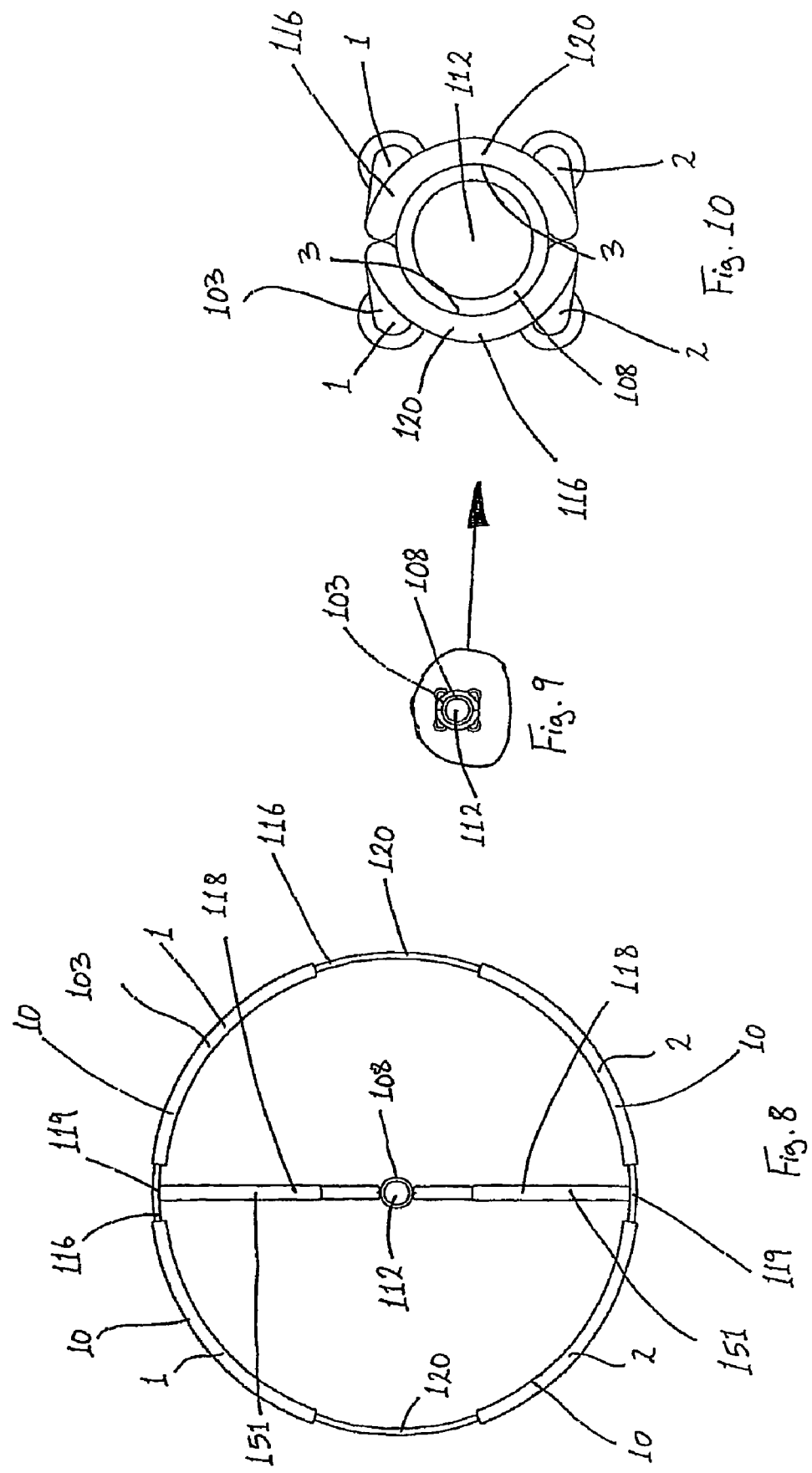

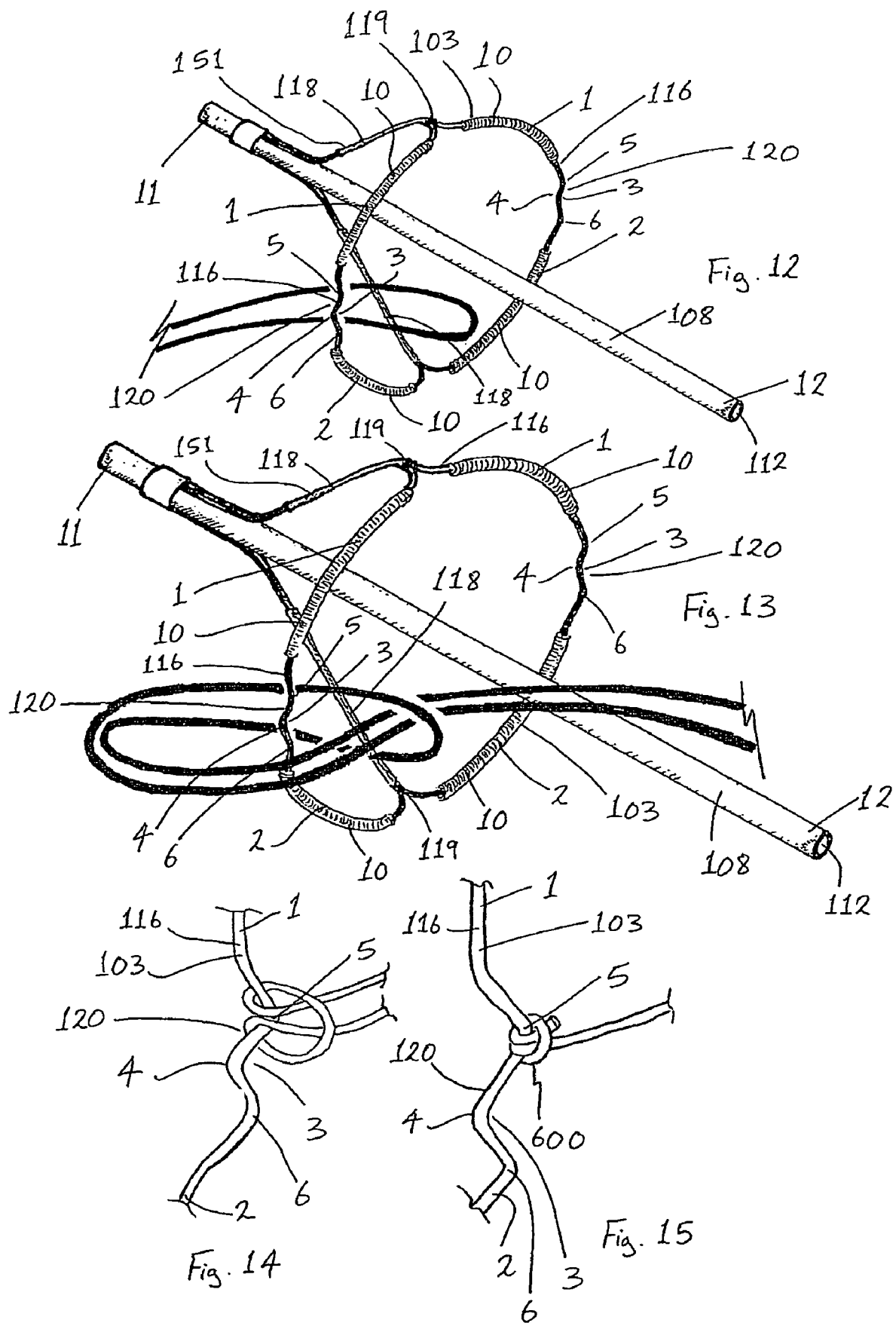

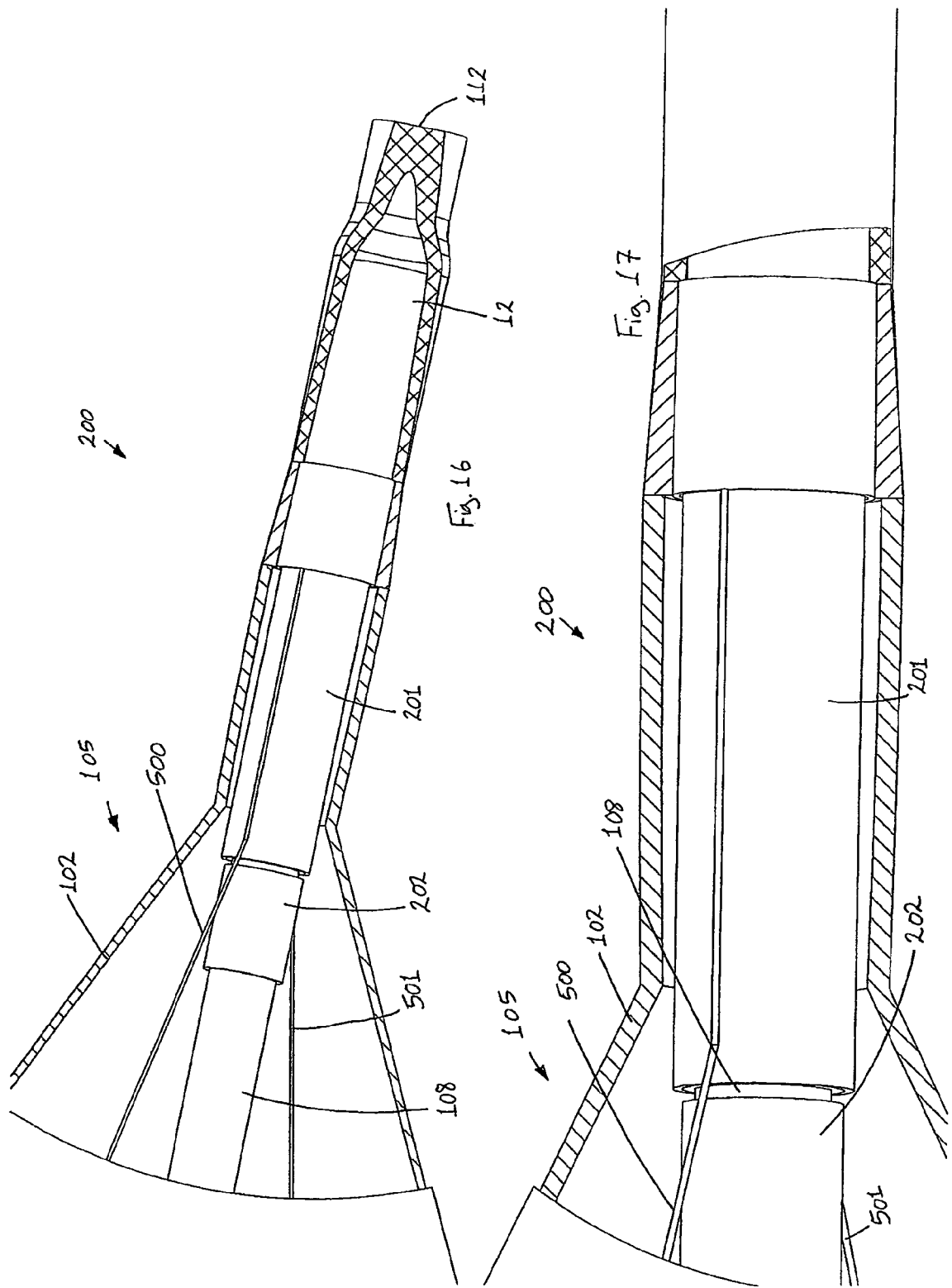

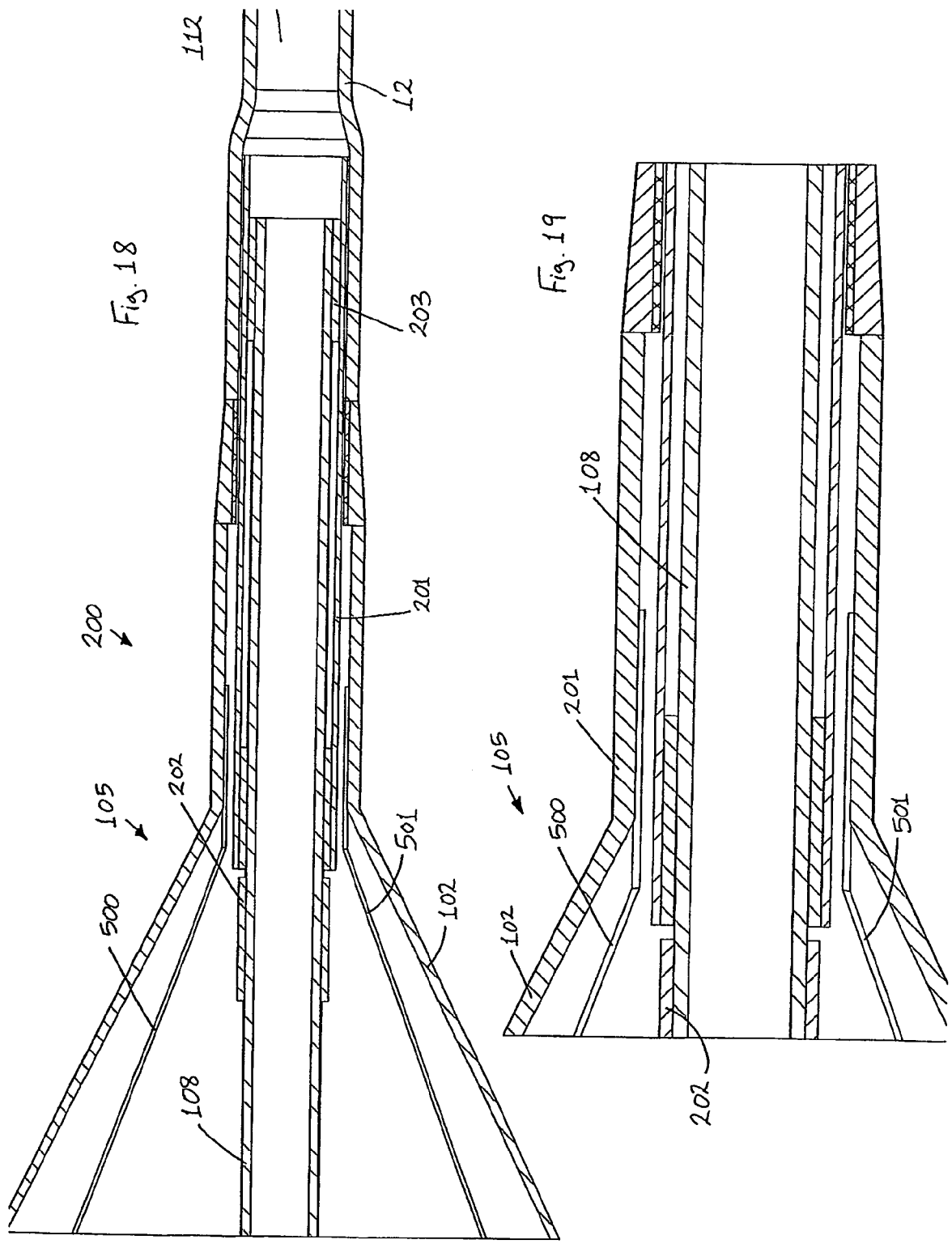

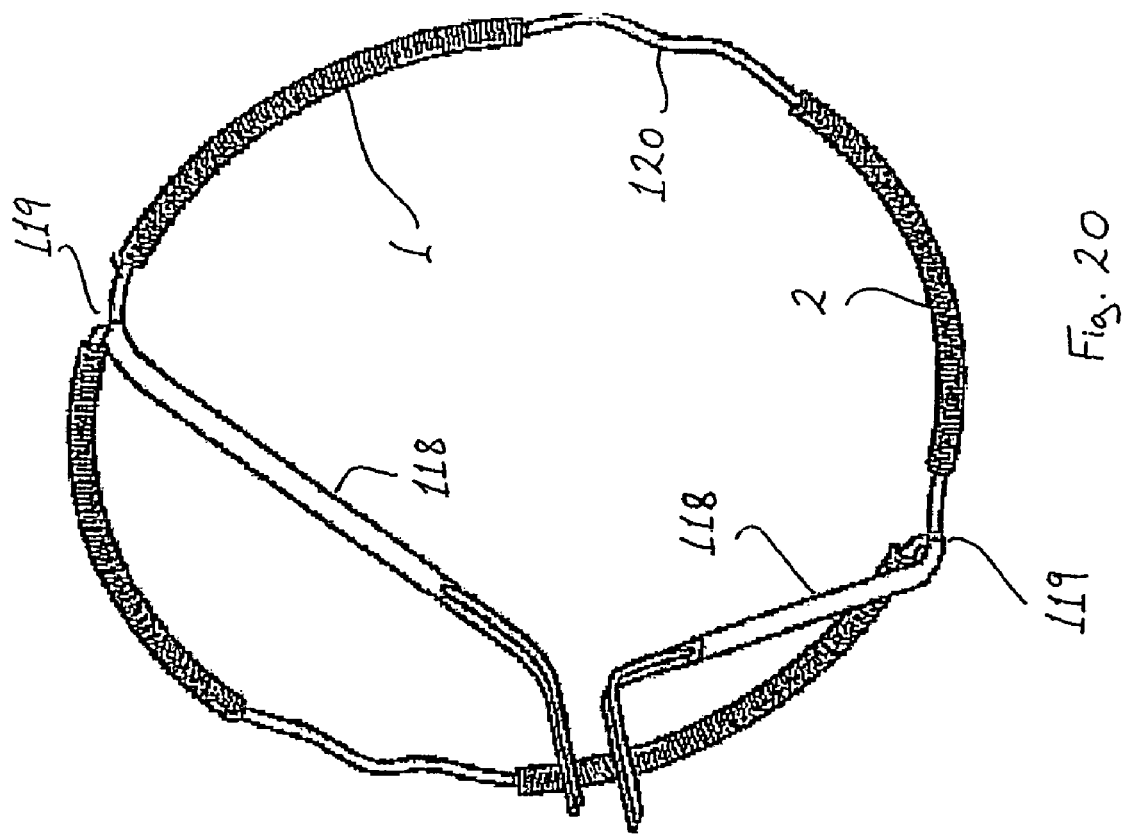
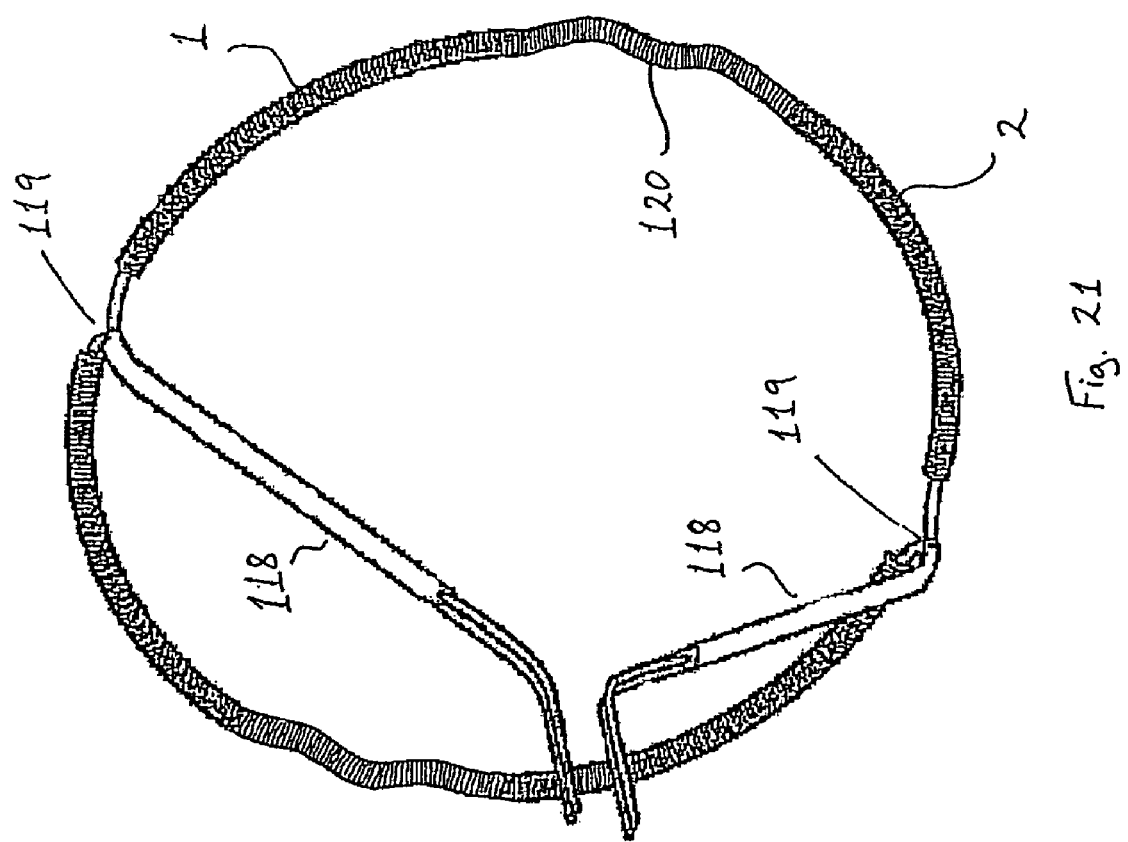

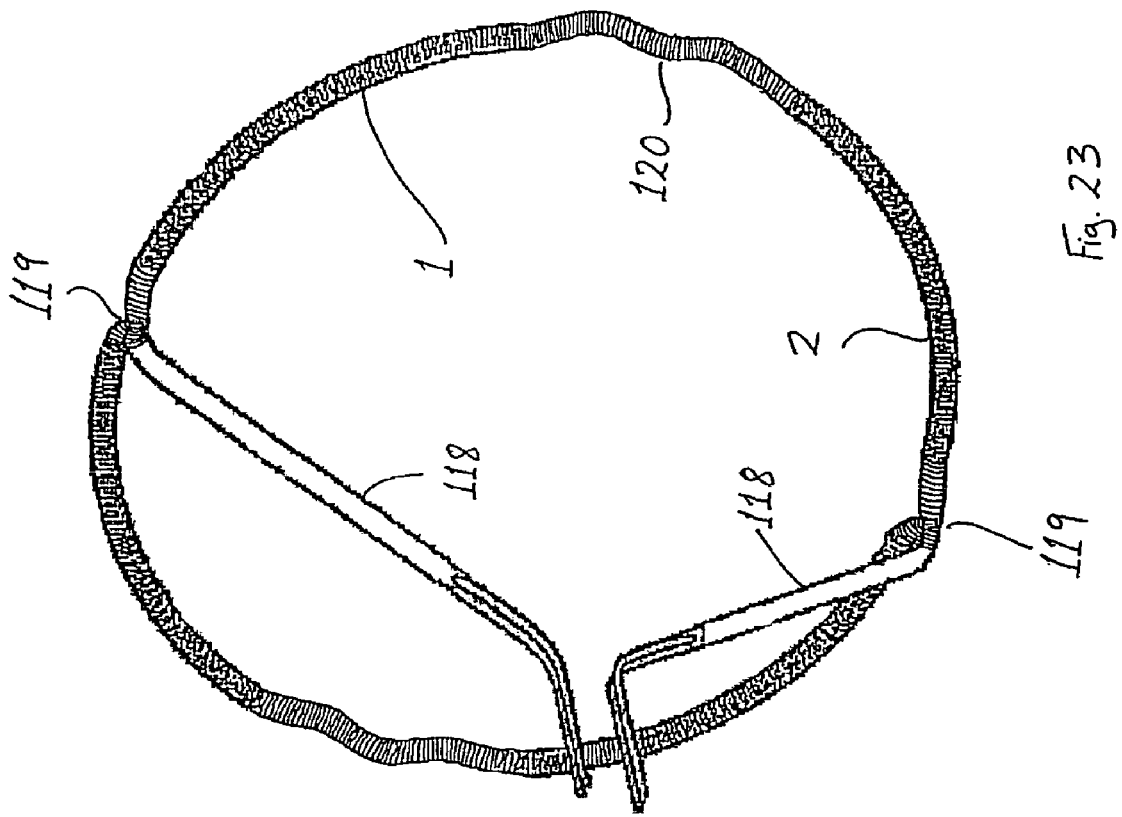
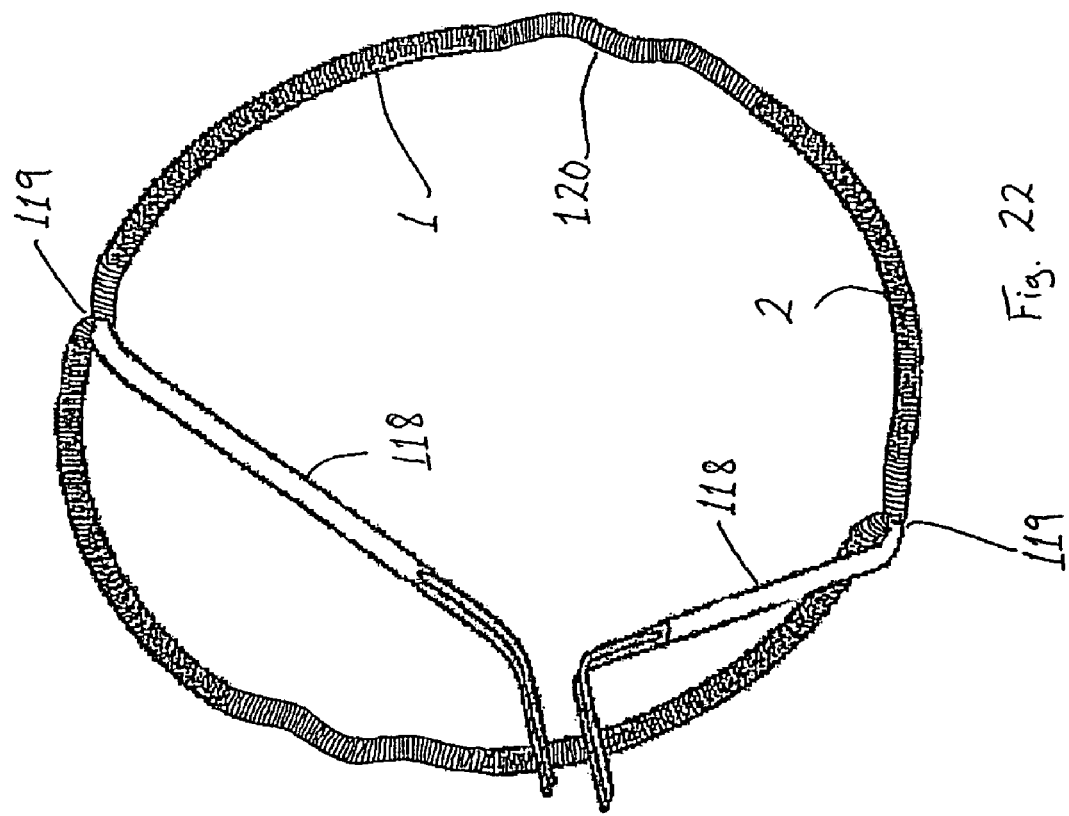

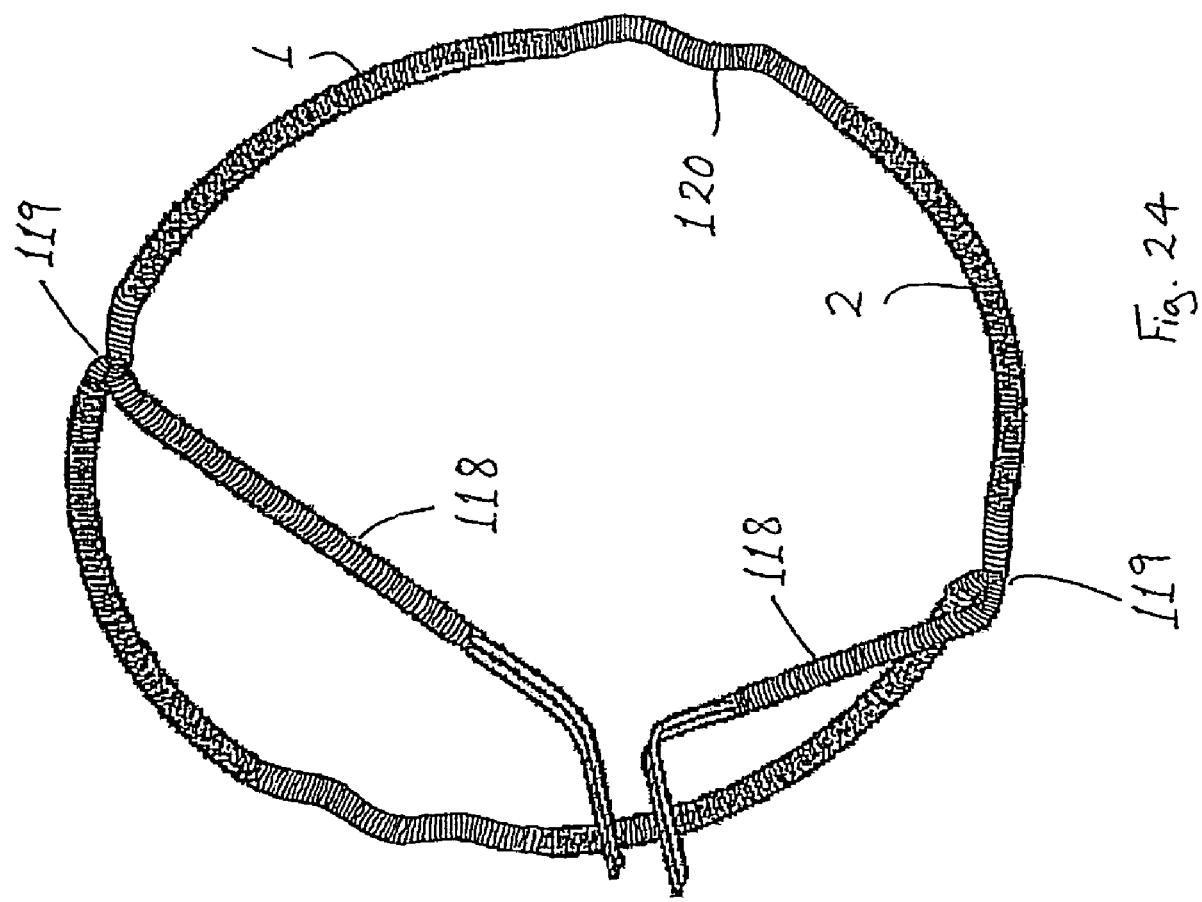

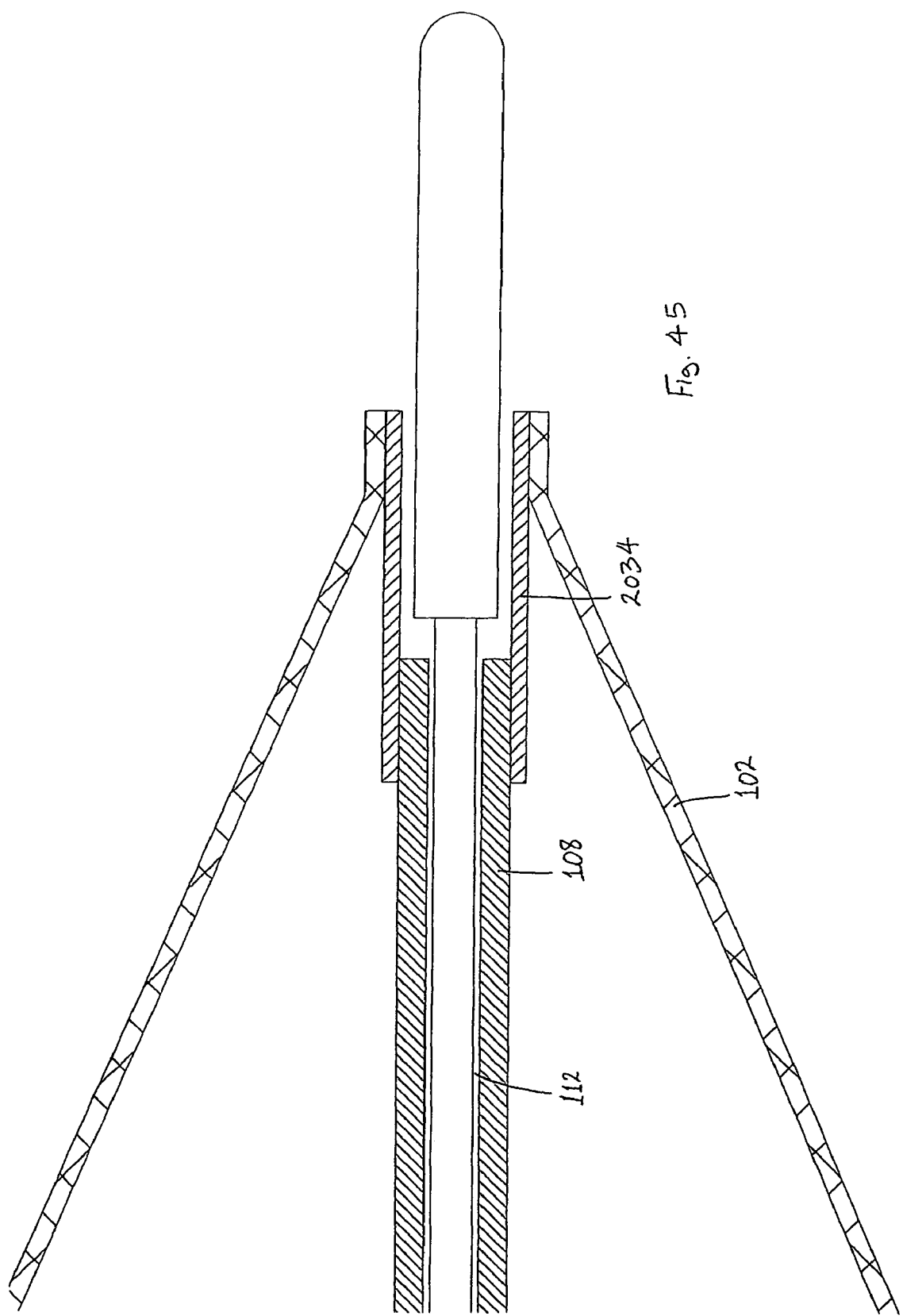

EMBOLIC PROTECTION DEVICE

RELATED APPLICATION

This application claims the benefit of U.S. patent application Ser. No. 60/672,432, filed Apr. 18, 2005, the entire teachings of which are incorporated herein by reference.

INTRODUCTION

This invention relates to an embolic protection device. In particular, it relates to an embolic protection device of the type comprising a collapsible filter body to capture embolic material, and a filter support to maintain the filter body in an expanded configuration when the embolic protection device is deployed in a vasculature.

Embolic protection devices of this general type are known. However, there exist a number of problems with some of the known embolic protection devices. In particular, upon collapse of the filter support, prior to delivery of the embolic protection device into and/or retrieval from a vasculature, large localised stresses may be induced in the filter support. Solutions to this problem heretofore may result in features which inhibit the optimum performance of the embolic protection device. In some systems flow paths for blood can develop between the filter body and the interior wall of the vasculature. In general conventional embolic protection devices are not highly trackable because of their length in the collapsed delivery configuration.

There is therefore a need for an embolic protection device which overcomes at least some of the disadvantages that exist with some of the known devices.

STATEMENTS OF INVENTION

According to the invention there is provided an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet opening sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising a plurality of segments, at least some of the segments being interconnected by a strain distributing linking element;
  in the collapsed configuration, the strain distributing linking element defining a low-profile relative to a carrier.

The linking element provides a means of distributing strain. In particular the linking element enables a point of inflection to be provided without adversely effecting the radial force and the integrity of the filter support.

The linking element also enables the collapsed filter support to adopt an efficient, low-profile configuration around the carrier, without applying undesirable compressive force to the carrier. Such undesirable compressive forces could otherwise potentially hinder movement of the embolic protection device relative to, for example, a guidewire.

In one embodiment of the invention in the collapsed configuration, the strain distributing linking element wraps around at least part of a carrier. The strain distributing linking element may extend circumferentially around at least part of a carrier. The strain distributing linking element may be at least partially curved, in the collapsed configuration a concave portion of the curve facing radially inwardly. The radius of curvature of the concave portion of the curve may be approximately equal to an external radius of a carrier. In the extended outwardly projecting configuration, the concave portion of the curve may face longitudinally. In the extended outwardly projecting configuration, the concave portion of the curve may face distally.

In another embodiment the filter support comprises a first segment and a second segment, the first segment being located adjacent to the second segment and being connected to the second segment by the strain distributing linking element, in the extended outwardly projecting configuration, the axis of the first segment being substantially aligned with the axis of the second segment. In the extended outwardly projecting configuration, the aligned axes of the first and second segments may intersect the concave portion of the curve. In the extended outwardly projecting configuration, the inner part of the concave portion of the curve may be located to one side of the aligned axes of the first and second segments, and the outer ends of the concave portion of the curve may be located to an opposite side of the aligned axes of the first and second segments. In the extended outwardly projecting configuration, the inner part of the concave portion of the curve may be located proximally of the aligned axes of the first and second segments, and the outer ends of the concave portion of the curve may be located distally of the aligned axes of the first and second segments. In the collapsed configuration, the axis of the first segment may be out of alignment with the axis of the second segment. The strain distributing linking element may undergo a shape change from a first shape in the extended outwardly projecting configuration to a second shape in the collapsed configuration to accommodate the change in alignment of the first and second segments. The strain distributing linking element may undergo a rotation from the extended outwardly projecting configuration to the collapsed configuration to accommodate the change in alignment of the first and second segments.

In another embodiment in the extended outwardly projecting configuration, the strain distributing linking element defines a first plane and the segments define a second plane substantially perpendicular to the first plane.

The strain distributing linking element may have a substantially sine-wave shape. The strain distributing linking element may have a substantially "M" shape.

In one embodiment each segment has a termination, and the terminations of adjacent segments are fixedly attached to one another along the length of the terminations, and extend generally parallel. The filter support may comprise a fixing element extending along at least part of the terminations to fixedly attach the terminations to one another. The fixing element may comprise a sleeve extending along at least part of the terminations. The terminations may extend generally axially.

In another embodiment the filter support comprises a radiopaque element extending along at least part of the support. The radiopaque element may comprise a radiopaque coil wrapped around the support. The radiopaque element may extend along at least part of the segment. The radiopaque element may extend along substantially the entire length of the segment. The radiopaque element may terminate at substantially the connection of the segment to the strain distributing linking element. The radiopaque element may extend along at least part of the strain distributing linking element.

In a further embodiment the filter support comprises a support frame, and at least one support leg, in the extended outwardly projecting configuration the support leg extending radially inwardly from the support frame. The cross-sectional configuration of the support leg may vary along the length of the support leg. The support leg may have a substantially circular cross-section at a first region of the support leg. The support leg may have a substantially flattened cross-section at a second region of the support leg. A short dimension of the flattened cross-section may be aligned substantially radially.

In one embodiment the filter element comprises the carrier. A proximal end of the carrier may be located proximally of the inlet end of the filter body. A distal end of the carrier may be located distally of the outlet end of the filter body. The carrier may be provided separate from the filter support. The carrier may comprise a tubular member. The carrier may be movable relative to a guidewire. The carrier may be slidable relative to a guidewire. The carrier may be rotatable relative to a guidewire. The carrier may comprise a guidewire.

In another embodiment the filter support comprises a support frame, and a flexible tether extending between the support frame and a carrier. The tether may be slidably coupleable to a carrier. The tether may be attached to a sleeve slidably mountable to a carrier. A carrier may have one or more limiting elements to limit the extent of sliding of the sleeve along the carrier. The tether may be attached to the support frame at the strain distributing linking element. The tether may have a taut configuration in the extended outwardly projecting configuration. The tether may have a slack configuration in the collapsed configuration. The tether may be substantially folded down in the collapsed configuration. The tether may comprise a wire.

In a further embodiment the filter support comprises two strain distributing linking elements, and in the collapsed configuration the strain distributing linking elements are longitudinally offset. In the collapsed configuration, a first strain distributing linking element may be located distally of a second strain distributing linking element. In the extended outwardly projecting configuration, the strain distributing linking elements may be longitudinally aligned. In the extended outwardly projecting configuration, a first strain distributing linking element may be located at substantially the same longitudinal region as a second strain distributing linking element. The filter support may comprise a first segment, a second segment, a third segment and a fourth segment, the first segment being located adjacent to the second segment and being connected to the second segment by a first strain distributing linking element, the third segment being located adjacent to the fourth segment and being connected to the fourth segment by a second strain distributing linking element, the length of the first and second segments being greater than the length of the third and fourth segments.

In one case the segment is of wire. The strain distributing linking element may be of wire. The segment may be of the same wire as the strain distributing linking element.

The at least one wire of the support frame may become torqued during collapse of the filter support. This torque induced upon collapse is evenly distributed along the wire without resulting in stress concentrations on the filter support. Thus, the wires may be of a small cross-sectional area which advantageously collapse down to a very low profile.

In addition, small wires enable greater flexibility for the filter element, which allow for ease of advancement through the vascular system.

The invention also provides in another aspect an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising a plurality of segments, at least some of the segments being interconnected by a strain distributing linking element;
  the strain distributing linking element being at least partially curved, in the extended outwardly projecting configuration the strain distributing linking element comprising a first convex portion and a second convex portion adjacent to the first convex portion.

In one embodiment of the invention in the extended outwardly projecting configuration, the convex portion faces longitudinally. In the extended outwardly projecting configuration, the convex portion may face distally.

In one case the strain distributing linking element comprises a connector portion between the first convex portion and the second convex portion. The connector portion may comprise a concave portion. In the extended outwardly projecting configuration, the concave portion may face longitudinally. In the extended outwardly projecting configuration, the concave portion may face distally.

In another aspect of the invention there is provided an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising: —
    a support frame; and
    a flexible tether;
    one end of the tether being attached to the support frame and the other end of the tether being attached to the filter body.

In one embodiment of the invention the proximal end of the tether is attached to the support frame. The distal end of the tether may be attached to the filter body. The tether may be fixedly attached to the support frame. The tether may be fixedly attached to the filter body. The filter body may be slidably coupleable to a carrier.

The tether acts to prevent any part of the support frame from inadvertently moving from within the filter body out through the inlet openings.

Because the tether is attached to the support frame and to the filter body, the tether acts to connect the filter body to the support frame. Thus if any part of the filter body were to become inadvertently damaged, for example the proximal part of the filter body, the filter body is prevented from breaking away from the filter element assembly due to the tether connecting the filter body to the support frame.

In another aspect the invention provides an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising: —
    a plurality of segments having terminations, the terminations of adjacent segments being fixedly attached to one another along the length of the terminations, and extending generally parallel; and
    a fixing element extending along at least part of the terminations to fixedly attach the terminations to one another.

The invention also provides in another aspect an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising a plurality of segments, at least some of the segments being interconnected by a strain distributing linking element, and a radiopaque element along at least part of at least one segment.

In another aspect of the invention there is provided an embolic protection device comprising: —
  a collapsible filter element for delivery through a vascular system of a patient;
  the filter element comprising a collapsible filter body and a filter support for the filter body;
  the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter support comprising: —
    a support frame; and
    a flexible tether extending between the support frame and a carrier, the tether being slidably coupleable to the carrier.

In another aspect the invention provides an embolic protection device comprising: —
  a collapsible filter element for delivery through a vascular system of a patient;
  the filter element comprising a collapsible filter body and a filter support for the filter body;
  the filter body having an inlet and an outlet end, the inlet end of the filter body having one or more inlet openings sized to allow blood and embolic material enter the body, the outlet end of the filter body having a plurality of outlet openings sized to allow through passage of blood but to retain undesired embolic material within the filter body;
  the filter support being movable between a collapsed configuration for movement through the vascular system, and an extended outwardly projecting deployed configuration to support the filter body in an expanded configuration;
  the filter element comprising a plurality of segments, at least some of the segments being interconnected by two strain distributing linking elements;
  in the collapsed configuration, the strain distributing linking elements being longitudinally offset.

BRIEF DESCRIPTION OF THE DRAWINGS

The invention will be more clearly understood from the following description of some embodiments thereof, given by way of example only, with reference to the accompanying drawings, in which: —

FIGS. 1 and 1(a) are perspective views of an embolic protection device according to the invention;

FIG. 1(c) is a cross-sectional, side view of a part of the device of FIG. 1;

FIGS. 1(d) and 1(e) are views similar to FIG. 1(c) of parts of another embolic protection device according to the invention;

FIGS. 1(f) and 1(g) are views similar to FIG. 1(c) of parts of a further embolic protection device according to the invention;

FIGS. 2 and 3 are perspective views of a filter support of the device of FIG. 1;

FIG. 4 is an end view from the proximal end of the filter support of FIGS. 2 and 3;

FIGS. 5(a) to 7(a) are perspective views of the filter support moving from the extended outwardly projecting deployed configuration to the collapsed configuration;

FIGS. 5(b) to 7(b) are side views of the carrier and the filter support moving from the extended outwardly projecting deployed configuration to the collapsed configuration;

FIG. 8 is an end view from the distal end of the filter support and carrier of FIG. 5 in the extended outwardly projecting deployed configuration;

FIG. 9 is an end view from the distal end of the filter support and carrier of FIG. 7 in the collapsed configuration with the same scale as FIG. 8;

FIG. 10 is an enlarged, end view from the distal end of the filter support and carrier of FIG. 7 in the collapsed configuration;

FIGS. 12 to 15 are perspective views illustrating attachment of a tether to a filter support of another embolic protection device according to the invention;

FIG. 16 is a perspective view of a distal end of the device of FIGS. 12 to 15;

FIG. 17 is an enlarged, perspective view of the distal end of the device of FIG. 16;

FIG. 18 is a cross-sectional, side view of the distal end of the device of FIG. 16;

FIG. 19 is an enlarged, cross-sectional, side view of the distal end of the device of FIG. 16;

FIGS. 20 to 32 are views of filter supports of further embolic protection devices according to the invention;

FIGS. 42 to 45 are cross-sectional, side views of the distal end of another embolic protection device according to the invention.

DETAILED DESCRIPTION

Figure 5B:
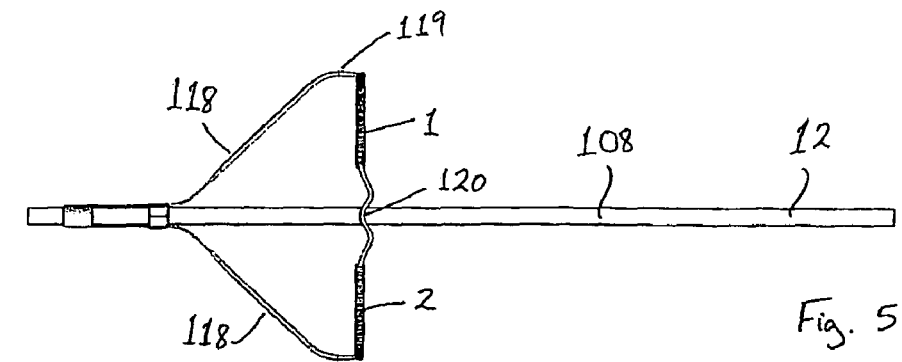
Figure 6B:
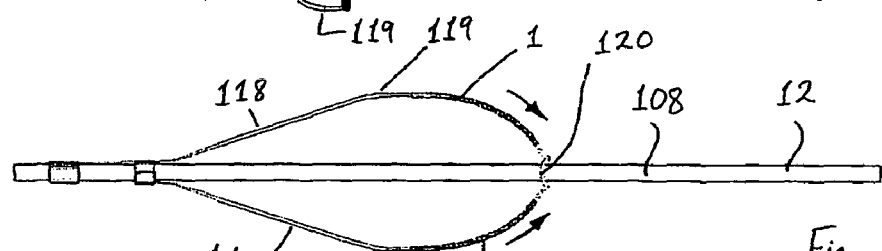
FIGS. 5 to 7 are plan views of a carrier of the device of FIG. 1 and the filter support of FIGS. 2 and 3 moving from an extended outwardly projecting deployed configuration to a collapsed configuration.

Referring to the drawings and initially to FIGS. 1 to 10 thereof, there is illustrated an embolic protection device 100 according to the invention. The embolic protection device 100 comprises a collapsible filter element for delivery through a vascular system of a patient. The filter element comprises a collapsible filter body 102, a filter support 103 for the filter body 102, and a carrier which comprises in this case a tubular member 108 to which the filter support 103 is mounted.

The filter body 102 has an inlet end 104 and an outlet end 105. The inlet end 104 has one or more large inlet openings 106 which are sized to allow blood and embolic material enter the filter body 102. The outlet end 105 has a plurality of small outlet openings 107 which are sized to allow through passage of blood but to retain undesired embolic material within the filter body 102. In this way, the filter element captures and safely retains any undesired embolic material in the blood stream within the filter body 102 while facilitating continued flow of blood through the vascular system. Emboli are thus prevented from flowing further downstream through the vascular system, which could otherwise have potentially catastrophic results.

The filter body 102 may be of an oriented polymeric material, such as that described in WO 01/97714A and US 2002/0042627A, the relevant contents of which are incorporated herein by reference.

Figure 1A:
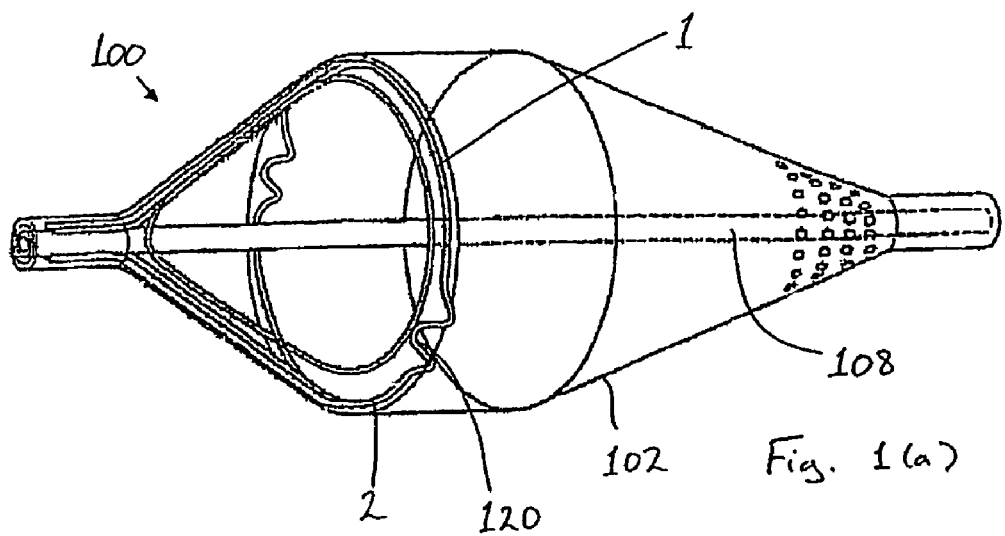

The diameter of each outlet opening 107 may be constant through the thickness of the filter body 102, as illustrated in FIG. 1(c).

Alternatively each outlet opening 107 may taper radially outwardly in a linear manner, as illustrated in FIGS. 1(d) and 1(e).

The thickness of the filter body 102 may vary along the length of the filter body 102. For example, the filter body 102 may have a larger thickness at the outlet end 105 (FIG. 1(d)) than at the intermediate portion between the inlet end 104 and the outlet end 105 (FIG. 1(e)).

As a further alternative, each outlet opening 107 may taper radially outwardly in a curved manner, as illustrated in FIGS. 1(f) and 1(g).

The material thickness of the filter body 2 may vary longitudinally to impart strength and low profile where desired.

The tapered lead out may act to prevent turbulent flow. Laminar flow may impart lower stress levels in blood and thus prevent blood clotting (FIGS. 1(d) and 1(e)).

Similarly the rounded lead out may act to prevent turbulent flow. Laminar flow may impart lower stress levels in blood and thus prevent blood clotting (FIGS. 1(f) and 1(g)).

The inner carrier tube 108 in this case extends longitudinally through the filter body 102 from a proximal end 11 proximal of the inlet end 104 to a distal end 12 distal of the outlet end 105.

The inner tube 108 has a guidewire lumen 112 extending therethrough, through which a guidewire may pass for exchange of the filter element over the guidewire. In particular the inner tube 108 is slidable and rotatable relative to the guidewire.

The filter support 103 in this case comprises two round wires 116 which extend from a proximal end 109. The wires 116 extend together axially and radially outwardly in a leg 118 from the proximal end 109, where the wires 116 are fixed to the inner tube 108, to a proximal termination point 119 where the wires 116 separate and extend circumferentially around to form a support frame hoop. The junction of the leg 118 with the support frame hoop is referred to in this specification as the proximal termination point 119. The length of each wire 116 around the support frame hoop is equal. From the proximal termination point 119 along the leg 118, the wires 116 are fixed to each other along the length of the leg 118, and extend generally axially and parallel in a bi-filar arrangement.

Each wire 116 has a strain distributing linking element. In this case the linking element comprises an "M"-shaped curve 120 in each wire 116. As each wire 116 extends around the frame support hoop, each wire 116 defines a first wire segment 1, a curve 120 and a second wire segment 2. Each curve 120 has a concave portion 3 with an inner part 4 and two outer ends 5, 6. Each of the outer ends 5, 6 forms a convex portion.

Each curve 120 connects the first segment 1 of the wire 116, which extends between the proximal termination point 119 and the curve 120, to the second segment 2 of the wire 116, which extends from the curve 120 to the other proximal termination point 119. Each curve 120 is formed integrally with the segments 1, 2 in the wire 116.

The wires 116 are preferably of a self-expanding material, such as Nitinol.

The filter support 103 is movable between a low-profile, collapsed configuration for movement through the vascular system, and an extended outwardly projecting deployed configuration. In this outwardly projecting configuration, the filter body 102 is supported in an expanded configuration by the filter support 103, so as to maximise the internal volume of the filter body 102 to capture and safely retain as much embolic material as possible. This arrangement of the circumferential support hoop formed by the wires 116 ensures that in the expanded position, the filter body 102 is supported by the filter support 103 in circumferential apposition with the interior wall of the vasculature.

In the extended configuration, the round wires 116 extend circumferentially around the M-shaped curve 120 in a sine-wave like pattern. This configuration increases the area of contact between the wires 116 and the filter body 102. This increased area of contact assists in more evenly distributing the radial forces from the support wires 116 to the filter body 102 and hence to the vessel wall. In this way, the risk of vessel trauma due to the forces exerted by the filter support 103 is minimised.

The proximal end 109 of the filter support 103 is fixed to the inner tube 108. Upon collapse of the filter element, the proximal end of the filter support 103 remains fixed relative to the inner tube 108, and the filter support 103 collapses distally against the inner tube 108. In this collapsed position, the filter support 103 is axially elongated relative to the expanded position.

Figure 5:
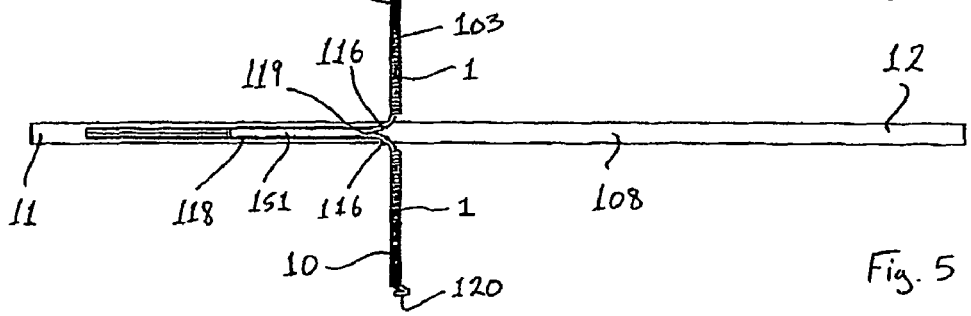
Figure 6:
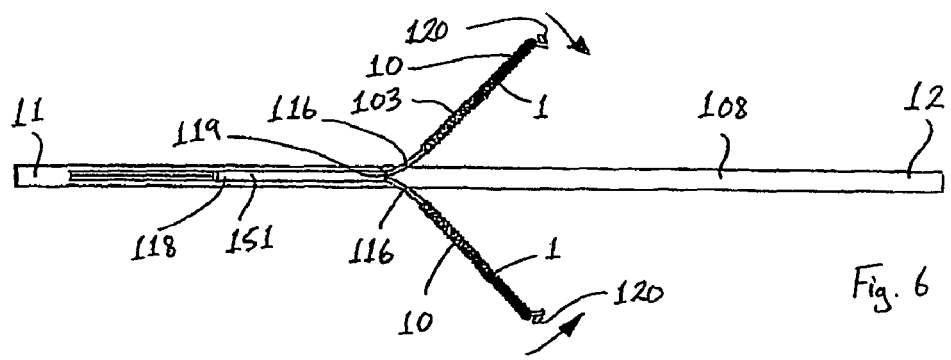
Figure 5A:
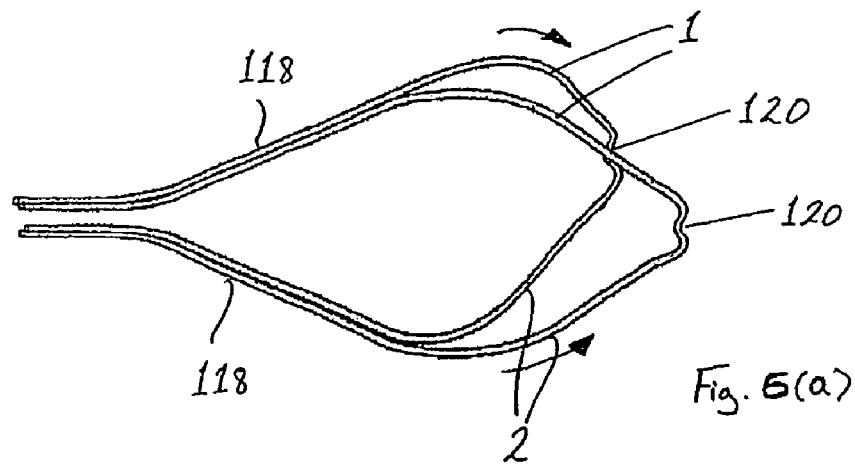
Figure 5A:
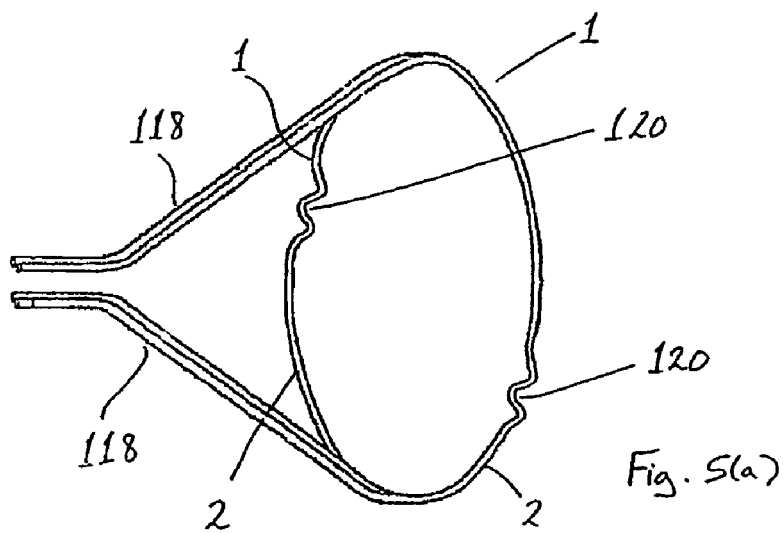

In the extended configuration (FIGS. 5, 5(a) and 5(b)), the longitudinal axis of the first segment 1 is parallel to and aligned with the longitudinal axis of the second segment 2. The segments 1, 2 together define a substantially circular plane perpendicular to the longitudinal axis of the inner tube 108.

In the extended configuration, the inner part 4 of the concave portion 3 is located proximally of the aligned axes of the segments 1, 2 of the hoop, and the outer ends 5, 6 are located distally of the aligned axes of the segments 1, 2. In this way, the aligned axes of the segments 1, 2 intersect the concave portion 5 of the curve 120, when the filter support 103 is in the extended configuration. In the extended configuration (FIGS. 5 and 5(a)), the concave portions 3 of the curves 120 face longitudinally in the distal direction, and the curves 120 define a plane which is substantially tubular. The tubular plane defined by the curves 120 is substantially perpendicular to the circular plane defined by the aligned segments 1, 2.

Similarly in the extended configuration (FIGS. 5 and 5(a)), the convex portions 5, 6 of each curve 120 face longitudinally in the distal direction.

It is noted that if the embolic protection device 100 were deployed in a smaller diameter vasculature, the deployed filter support 105 may not assume the fully extended configuration of FIG. 5. In such a case, the longitudinal axis of the first segment 1 may not be parallel to and aligned with the longitudinal axis of the second segment 2, when deployed.

Figure 7B:
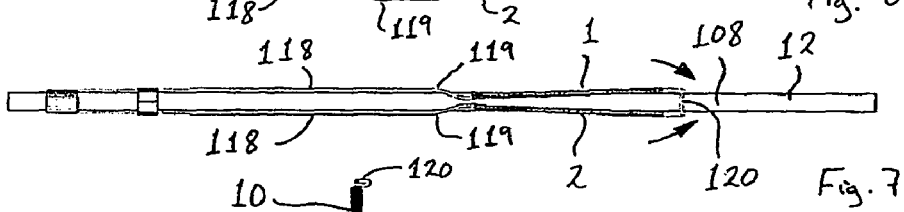

In the collapsed configuration, the longitudinal axis of the first segment 1 is out of alignment with the longitudinal axis of the second segment 2. Both segments 1, 2 extend substantially parallel to the longitudinal axis of the inner tube 108 along the external surface of the inner tube 108. To accommodate the change in alignment of the segments 1, 2, the curve 120 undergoes a shape change and rotates as the filter support 103 moves from the extended configuration to the collapsed configuration. In the collapsed configuration (FIGS. 7, 7(a), 7(b)) the concave portion 3 of the curve 120 faces radially inwardly towards the inner tube 108. In addition the radius of curvature of the concave portion 3 of the curve 120 is approximately equal to the external radius of the inner tube 108, such that in the collapsed configuration the curve 120 wraps around part of the inner tube 108, as illustrated in FIG. 10. In particular, in the collapsed configuration, the curve 120 extends circumferentially around approximately 180° of the circumference of the inner tube 108 (FIG. 10). In this manner, the curve 120 and the filter support 103 in general define a very compact, low-profile relative to the inner tube 108, when the filter support 103 is in the collapsed configuration. The curve 120 is shaped to minimise and preferably to eliminate any impingement of the collapsed curve 120 on the inner tube 108.

As the filter support 103 collapses down against the inner tube 108, the wires 116 become torqued. This torqueing action is similar to the process of elongation of a coiled spring. Because the support frame 103 is defined by round wires 116, the torque developed in each wire 116 will be evenly distributed along the length of each wire 116. In addition, the bi-filar connection of the wires 116 to each other at the termination point 119, further assists in torque distribution along the wires 116. Thus, collapse of the filter support 103 does not induce high, localised stresses in the filter support 103. In this way, the filter support 103 may be constructed of wires 116 of a small cross-sectional area which will collapse down to a very low profile. Furthermore, the collapsed filter element with small wires 116 has greater flexibility for ease of advancement of the filter element through the vascular system.

Each leg 118 has a proximal portion 800 which extends substantially parallel to the inner tube 108 and a distal portion 801 which extends radially outwardly to the proximal termination point 119.

The two wires 116 have an elongate cross-section, in this case a rectangular cross-section, at the proximal end 109 of the leg 118 and have a circular cross-section along the support frame hoop. The wires 116 are arranged such that the shorter dimension of the rectangle is aligned along the radial direction of the filter support 103. At the proximal end of the distal portion 801, the cross-sectional configuration of the leg 118 varies from the rectangular cross-section to the circular cross-section.

This flattened wire configuration at the proximal end 109 provides for a filter support 103 with enhanced flexibility. This is achieved because the second moment of area of the wires 116 is reduced in the flattened configuration.

In addition, the flattened wires 116 minimise the influence of the support leg 118 on the outward radial force exerted by the support frame 103. This results in a filter support 103 which exerts a relatively constant outward radial force around the circumference of the filter support 103.

To enhance visualisation of the filter element, a radiopaque coil 10 is wrapped around each wire segment 1, 2. Each coil 10 extends along the entire length of the segment 1, 2 and terminates at the point where the segment 1, 2 is connected to the curve 120.

An important influencing factor on the outward radial force exerted by the filter support 103 on the filter body 102 is the fixing of the wires 116 relative to one another at the proximal termination points 119 and/or at the distal termination points 120. It may be advantageous to securely fix the wires 116 relative to one another at the proximal termination point 119 to achieve the required radial force perpendicular to the proximal termination point 119.

One means of fixing the two wires 116 of the filter support 103 relative to one another at the proximal termination point 119 and along the leg 118 is to clamp the wires 116 together using a tubular polymeric covering sleeve 151, as illustrated in FIG. 2. The sleeve 151 extends along the leg 118 and is heat-sealed around the leg 118. In this way, the sleeve 151 provides a durable means of fixing the wires 116 together which will effectively resist peeling of the wires 116 apart, thus resulting in a highly robust filter element.

The sleeve 151 may be partially of a radiopaque material, such as platinum, or iridium, to provide visualisation of the filter element during use.

Another suitable means of fixing the two wires 116 together is to directly solder, weld or bond the two wires 116 together.

It will be appreciated that a variety of different means may be used to effectively fix the wires 116 relative to one another at the proximal termination point 119 and/or at the distal termination point 120.

Figure 7:
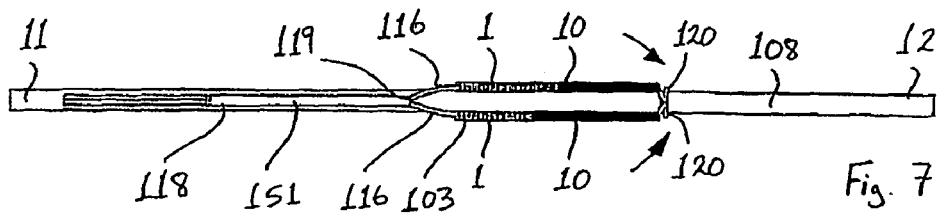
Figure 7A:
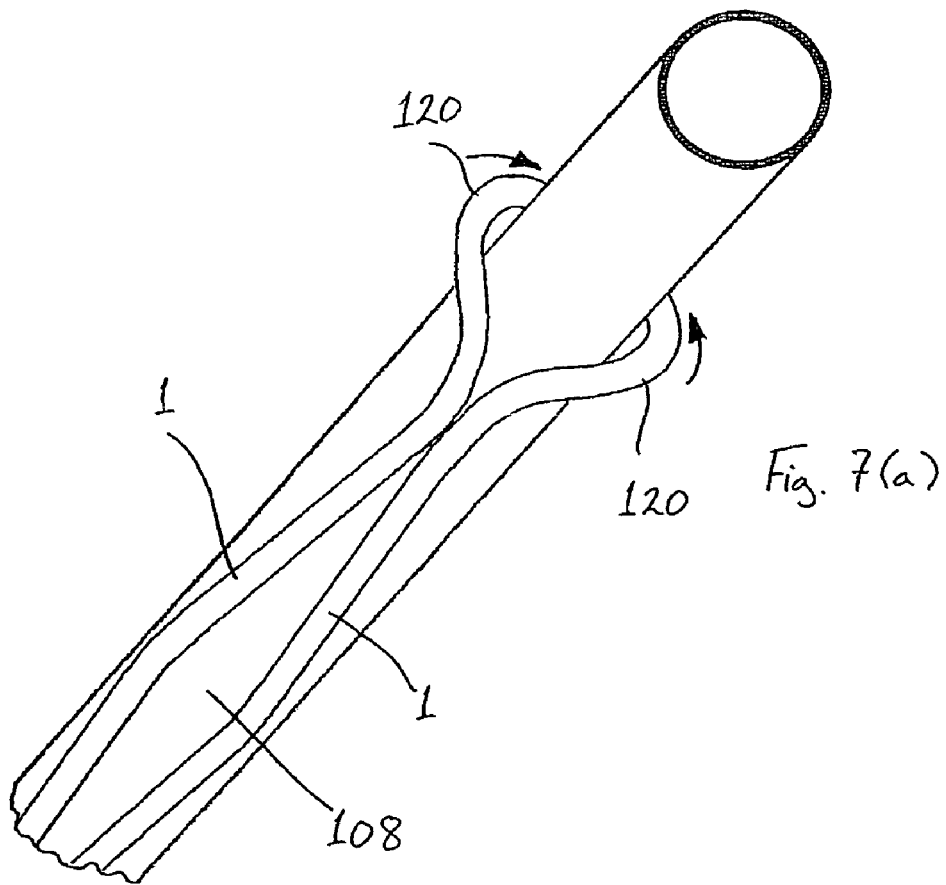

The curve 120 acts as a strain reliever or distributor when the wires 116 are wrapped down, as illustrated in FIG. 7. The curve 120 has a relatively large radius resulting in highly efficient strain distribution. In addition, the curve 120 allows the support frame 103 to accommodate varying vessel contours and sizes. In effect the curve 120 acts as a diameter or circumference adjuster allowing an embolic protection device to adapt to different vessel contours and sizes while maintaining apposition with the vessel wall. The strain relieving geometry of the curve 120 enhances the compliance of the bend points without creating a weakened hinge point, thus ensuring that there is no discontinuity in the circumferential seal against the vessel wall.

The curve 120 can also be regarded as a distal termination point. The curved termination 120 enhances the ability of the filter support 103 to be wrapped down to a low profile.

In addition, the curved configuration of the distal termination 120 spreads the force exerted by the filter support 103 on the filter body 102 over a greater area. In this way, the local pressures applied by the filter support 103 on the filter body 102 and the walls of a vasculature are more evenly distributed, this minimising the possibility of vessel trauma.

Another important advantage of the strain distributing features, such as the curves 120, is that they provide an anchor to which connecting elements such as tethers may be readily attached, as described in more detail below.

The radial forces exerted by the filter support 103 on the filter body 102 and the walls of a vasculature depend on a number of factors, such as the diameter of the round wires 116, the material chosen for the wire 116 and the properties of that material, the number of wires 116 in the filter support 103, the angle of inclination of the support leg 118, and the radius of the bend 120 in the filter support 103. By suitably varying these factors, the radial force exerted by the filter support 103 may be accurately controlled.

Individual wires 116 may taper towards the proximal or distal end.

The support frame 103 may comprise a segmented ring or hoop which may have an elliptical cross-section in the free expanded state. The support ring may be angulated relative to the axis of the inner member 108.

In use, the filter element is collapsed down from the extended configuration to the collapsed configuration, and loaded into a delivery catheter with an associated torqueing of the wires 116 around the support frame hoop. The filter element is then delivered through a vasculature fixed to or over a guidewire using the delivery catheter until the filter element is located at a desired site in the vasculature.

By moving the delivery catheter proximally relative to the filter element, the element is deployed out of the delivery catheter at the desired site in the vasculature. The filter support 103 expands radially outwardly to support the filter body 102 in circumferential apposition with the interior wall of the vasculature. In the fully expanded position, the wires 116 of the support frame 103 are substantially free of torque.

The site of deployment of the filter element in the vasculature is typically downstream of a treatment site, such as a region of stenosis in the vasculature. During the performance of a treatment procedure, the filter element captures and safely retains any embolic material in the blood stream within the filter body 102.

After completion of the treatment procedure, the filter element is collapsed down from the extended configuration to the collapsed configuration, and retrieved into a retrieval catheter with any retained embolic material within the filter body 102. The wires 116 around the support frame 103 are again torqued during collapse. The retrieval catheter is then withdrawn from the vasculature with the filter element within the retrieval catheter.

The delivery, deployment and retrieval of the embolic protection device of the invention, as described above, is similar to that described in our WO 99/23976, WO01/80776A (US 2002-0052626A) and WO01/80773A (US 2002-0049467A), the relevant contents of which are incorporated herein by reference. The filter element may be slidably exchanged over the guidewire without any attachment means between the filter element and the guidewire. A distal stop on the guidewire assists in retrieval of the filter element. The guidewire may remain in the vasculature after retrieval of the filter element.

Figure 7C:
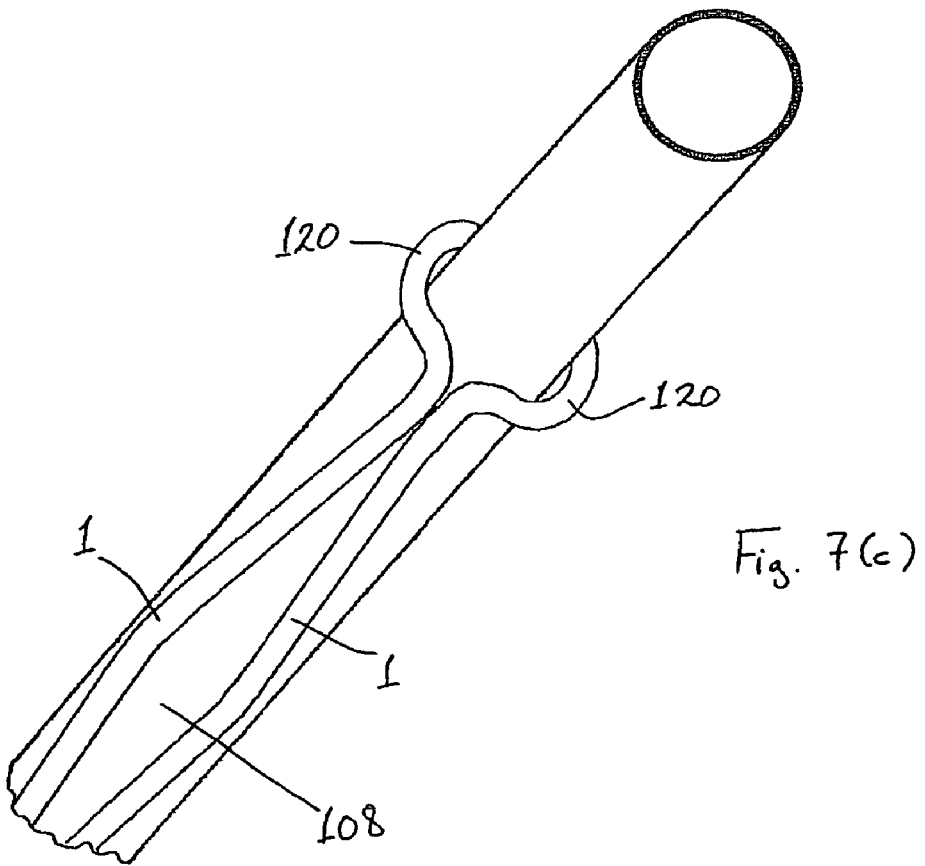
FIGS. 7(c) and 7(d) are perspective views of filter supports of other embolic protection devices according to the invention in the collapsed configuration.
Figure 7D:
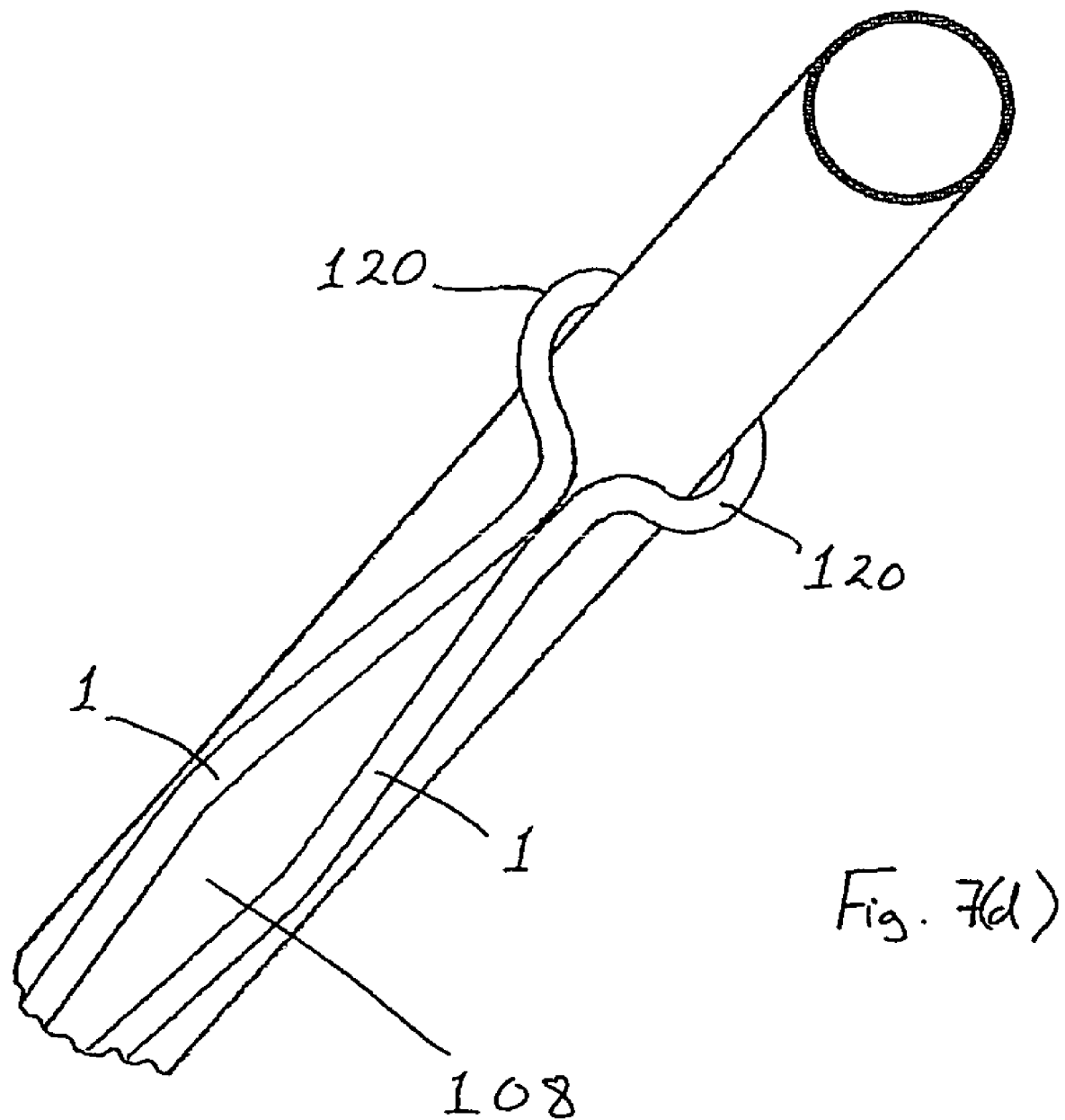

The extent to which the filter wraps down around the inner tube 108, may be controlled by controlling the configuration of the curve 120. For example as illustrated by comparing the filter of FIG. 7(a), with the filter of FIG. 7(c), with the filter of FIG. 7(d), the extent to which the curve 120 wraps down around the carrier 108 may be varied by varying the radius of curvature of the curve 120.

Figure 11:
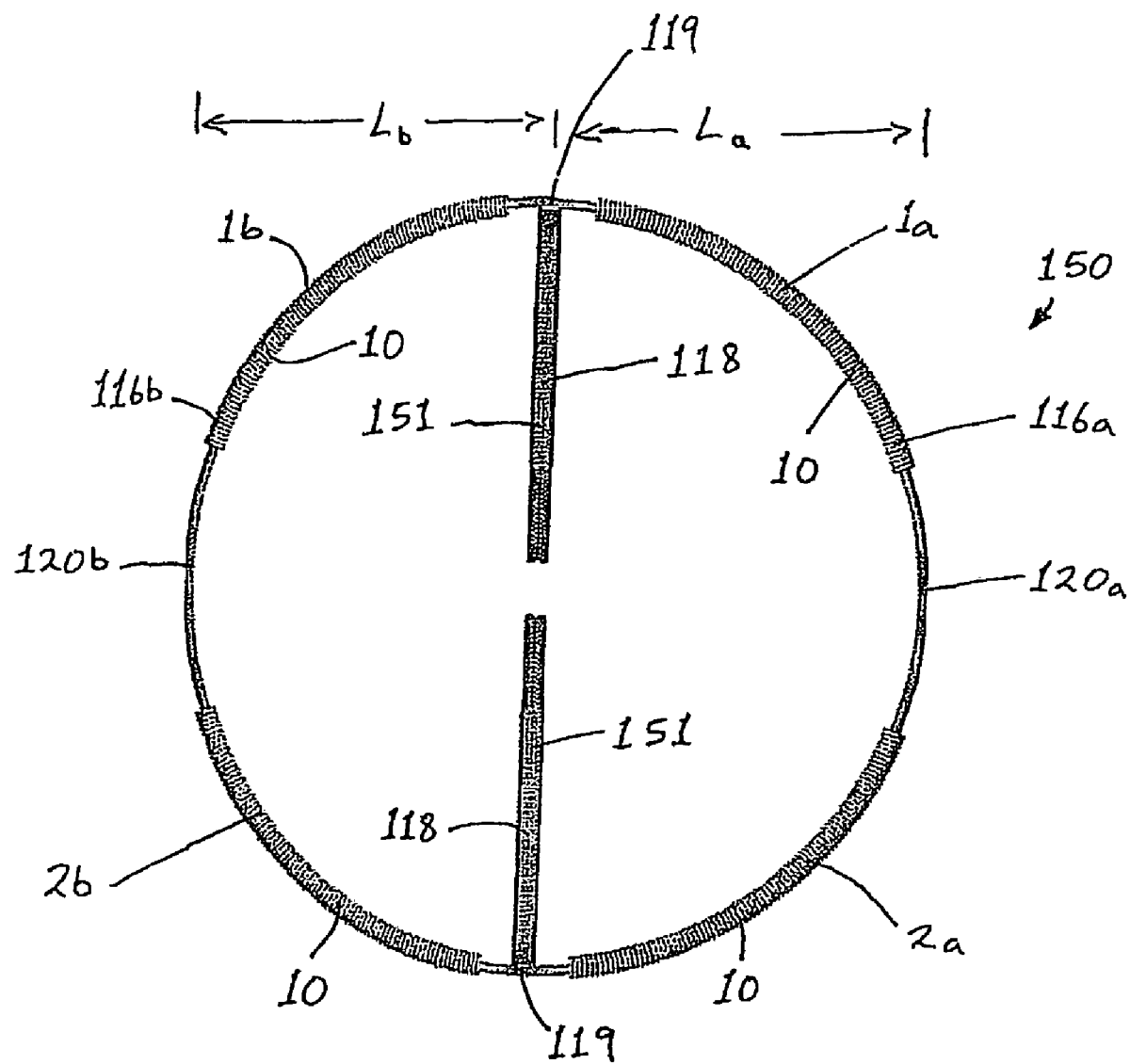
FIG. 11 is an end view from the proximal end of a filter support of another embolic protection device according to the invention.

In FIG. 11 there is illustrated a support frame 150 of another embolic protection device according to the invention, which is similar to the device 100 of FIGS. 1 to 10, and similar elements in FIG. 11 are assigned the same reference numerals.

In this case, one round wire 116a extends around the support frame hoop to define a first wire segment 1a, a curve 120a and a second wire segment 2a, and the other round wire 116b extends around the support frame hoop to define a first wire segment 1b, a curve 120b and a second wire segment 2b. As illustrated in FIG. 11, the combined length of the first segment 1a, the curve 120a and the second segment 2a of the wire 116a is greater than the combined length of the first segment 1b, the curve 120b and the second segment 2b of the wire 116b. In particular the length of the wire 116a is not equal to the length of the wire 116b. As a result the radius La of the support frame hoop defined by the wire 116a is greater than the radius Lb of the support frame hoop defined by the wire 116b. This arrangement results in the curves 120a, 120b being longitudinally offset when in the collapsed configuration. In particular the curve 120a is located distally of the curve 120b due to the greater radius La, when the filter support 103 is collapsed. Because the curves 120a, 120b are offset, this facilitates a better wrap-down of the filter support 103 around the inner tube 108.

It is noted that in the extended configuration, the curves 120a, 120b are longitudinally aligned with both curves 120a, 120b located at the same longitudinal region.

The filter support 103 comprises a segmented ring structure which has two circumferential wire segments 1,2. The wire segments 1,2 are connected by the strain distributing linking element 120 at one end and by the bifilar joint 119 at the other end. The bifilar joint 119 may be coupled to the carrier 108 by a single or multiple struts and/or tethers. In one case the strut is attached to the carrier 108. The connection may permit rotation, or longitudinal movement relative to the carrier 108 either distal or proximal to the point of attachment to the segmented ring.

In some cases the attachment to the carrier 108 is rigid, in other cases a flexible joint is provided using a tether, a loop, a thinned wire section or the like. A focal tether may be utilised. A focal tether implies that the strut has tensile and compressive integrity but the joint is not rigid. The joint can thus flex in all directions but it cannot translate.

The support frame 108 may have distal, proximal and/or intermediate anchors. One anchor may be fixed and another translatable and/or rotatable relative to the carrier 108. For example a proximal anchor may be translatable, or in arrangements in which both proximal and distal anchors are provided, both may be translatable.

Referring to FIGS. 12 to 19 there is illustrated another embolic protection device 200 according to the invention, which is similar to the device 100 of FIGS. 1 to 10, and similar elements in FIGS. 12 to 19 are assigned the same reference numerals.

The support frame 103 incorporates tethering for connecting the support frame 103 distally to the carrier 108. In this case the filter support 103 comprises two flexible tethers 500, 501 extending from the support frame hoop distally and radially inwardly towards the inner tube 108. The two distal tethers 500, 501 are used to connect the curve 120 to the tubular member 108. The proximal end of each tether 500, 501 is attached to the support frame hoop at each curve 120, and the distal end of each tether 500, 501 is attached to a sleeve 201. The sleeve 201 is slidably mounted to the inner tube 108. Two longitudinally spaced-apart stop elements 202, 203 on the inner tube 108 limit the extent of sliding of the sleeve 201 along the inner tube 108.

In the extended configuration, the tethers 500, 501 have a taut configuration (FIGS. 16 to 19). In the collapsed configuration, the tethers 500, 501 have a slack configuration and are substantially folded down.

The distal tethers 500, 501 provide added safety and stability to the support frame 103 without any increase in the length of the device 200 when wrapped down. The tethers 500, 501 may be of any suitable material such as fine gauge wire, for example Nitinol wire, fibre or polymers. The tethers 500, 501 may be of solid or braided construction, for example.

Referring to FIGS. 12 to 15 there is illustrated one type of knot 600 in the tether 500 being tied to the linkage element curve 120 of the support frame 103.

It will be appreciated that the carrier 108 may be provided as a separate component, such as guidewire, over which the embolic protection device may be exchanged.

The invention incorporates circumferential wire angulation into support structure design to give maximum circumferential support to the filter body.

The angulated hysteresis structure/cell configurations of the invention are particularly suitable as support structures because the strain energy is distributed over long lengths of the wire structure. The wrapping/loading mechanisms of these hysteresis structures are both a bending/straightening of the constituent wires as well as a twisting/torsion of the wires. The energy applied/introduced during the loading process is both bending and torsional strain energy. These energies due to their nature and the method by which the support structure folds/loads are distributed over long lengths of the wire as opposed to concentrated focal points so that the level of energy within the wire at any point does not exceed the elastic strain energy limits. Hysteresis designs optimise the strain distribution along the wire lengths. With these designs there is distributed bending and torsional strain along the wires. The component of radial force is converted to torque strain energy. The corollary of this principle, that the torsional strain energy provides radial stiffness, also applies.

Angulated hysteresis structures also enable large radial forces to be achieved from structures with small wire diameters. The reason for this is that these designs use a greater proportion of the wires' torsional strain resistance. The wires offer far greater resistance to torsional strain than to bending strain and therefore these designs optimise this feature. The angulated hysteresis structure design arranges the wires so that the load induces torsional strain and therefore delivers far higher performance with small wire diameters than those designs that rely on the bending strain/resistance.

The hysteresis support structure of the invention has section/s of wire curvature that can be defined in 3D planes. These sections of wire have geometrical properties such as a radius of curvature and a centre of radius of curvature. As the hysteresis structure designs are loaded and deployed, the geometrical properties of these sections change—that is the radius of curvature changes and the centre for the radius of curvature moves in a path that can only be defined within a 3D plane.

Even relatively simple hysteresis designs are made up of numerous sections of curvature with their corresponding radius of curvature joined end to end to form a complete hysteresis loop. These sections of curvature depending on the complexity of the design may be combinations of concave and convex elements/segments. The hysteresis loops themselves can be various shapes and there are multitudes of hysteresis loop/cell geometries.

A wire or laser cut support structure design based on a hysteresis cell type design typically may have four arms acting to provide uniform radial force to give good vessel apposition. In attempting to provide support over the complete body length structure designs tend to have multiple arms/cells providing the support. The problems with many of these designs is the excessive elongation associated with them during loading. The advantage with the invention in suit is that it only extends the same length whether one/two or multiple arms are used. The invention also lends itself to low wrapping profiles, because during loading it contracts both radially and circumferentially leaving parallel straight wires which often prove to be the easiest for loading.

Further advantages of the round wire arrangements include:

Using a round wire allows for substantially more of the strain energy induced during loading/wrapping down into a low profile to be stored as torque along the wire lengths. This means that the strain energy is more evenly distributed within the wires than with conventional section designs, in which the strain energy generally becomes concentrated around the bend points which can cause problems such as exceeding the elastic strain energy limit at these locations.

The invention also has the advantage of being more trackable and flexible. This design achieves this by allowing the structure to hinge at points. Planes through these points demonstrate that bending at these hinge points is very easy.

Furthermore, the radial force may be altered by:
a) changing the wire diameter;
b) changing the proximal and distal cone angles.

Points of stress concentration can become strained plastically and result in poor support structure performance.

Conventional approaches to dealing with these issues involve designing in strain distributing geometric features to spread these strains over a greater area of the structure. Another approach involves the use of thinning out sections in the area of high strain. At a given radius of curvature the strain in a thin section is less than that of a thick section. Thinning however compromises the overall support provided by the structure.

The filter support of the invention provides for torsional strain and thus eliminates the need to use section thinning or thickening to distribute strain.

When torque stresses are applied to members of an approximately circular cross section the resulting strain becomes distributed over the length of the section. In this situation it is not possible to generate a corresponding torque phenomenon to the cantilever bending phenomenon. The present invention provides elements which are torsionally strained in the collapsed configuration and which release these torsional strains as they expand.

When collapse strains are evenly distributed, it is possible that the overall level of strain in the system can be increased without inducing plastic deformation. This makes it possible to achieve a high level of radial support from small diameter support members.

Designs that induce torque-strain into the support structure during collapse are particularly advantageous. Bending strains tend very often to have a strong cantilever effect with the strain becoming localised at points of stress concentration.

The torque strain in the wire can be released in a variety of expansion pathways. This means that the release of the torque is not inhibited when uniaxial resistance is encountered. This feature helps the support structure deliver good apposition to eccentric vessels. This is an important aspect of the invention, especially when the filter is placed in diseased vessel segments.

The geometric configuration of the filter support aligns the wires of the cell in a substantially circumferential direction in the expanded state. This ensures that radial pressure applied by the vessel is initially transmitted as compressive hoop stress to the structure.

The compressive component of applied stress decreases as the system collapses, however the torsional resistance increases resulting in a relatively flatter loading stress curve.

It will be appreciated that the filter body may be attached to or independent of the filter support frame.

The radiopaque coil 10 may extend along the length of the segments 1, 2 terminating before the proximal termination points 119, and terminating at the point where the segments 1, 2 are connected to the curve 120 (FIG. 20). Alternatively the coil 10 may extend along the curve 120 (FIG. 21). As a further alternative the coil 10 may extend to the proximal termination point 119 (FIG. 22). In a further alternative the coil 10 may extend passed the proximal termination point 119 partially along the leg 118 (FIG. 23). Alternatively the coil 10 may extend along the full length of the leg 118 (FIG. 24). In this case the coil 10 may be used to fix the wires 116 together, and the sleeve 151 may not be required.

Figure 25:
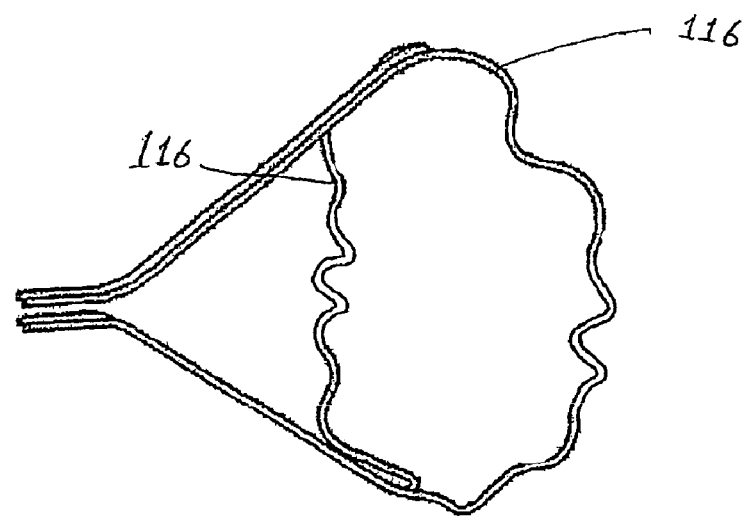

In the filter support of FIG. 25, the round wires 116 extend around the support frame in an irregular, wave-like pattern. This configuration increases the area of contact between the wires 116 and the filter body 102. In this way the risk of trauma due to the forces exerted by the filter support is minimised.

Figure 26:
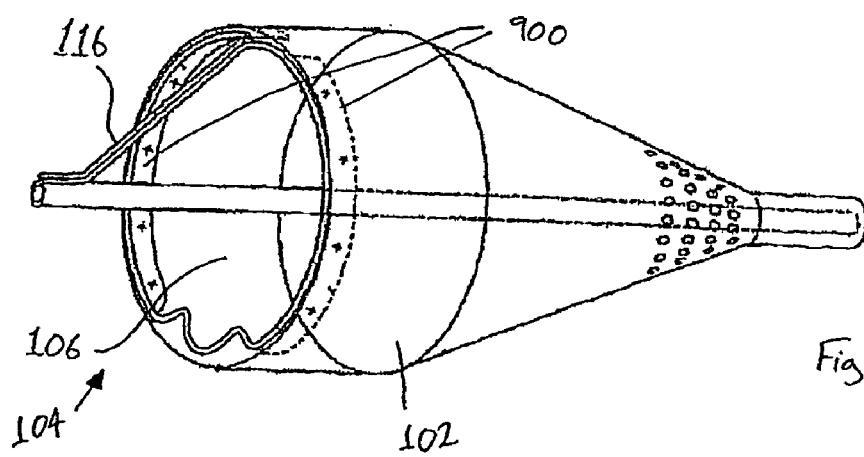

Another filter is illustrated in FIG. 26, and similar elements to those in previous drawing are assigned the same reference numerals. The filter support comprises a single round wire 116 which extends axially and radially outwardly in a single leg 118 to the proximal termination point 119. The wire 116 extends circumferentially fully around the support frame.

The filter body 102, has a single, large inlet opening 106 defined at the inlet end 104. This arrangement further minimises the possibility of any embolic material becoming caught or hung-up on any parts of the filter at the inlet end 104. This arrangement also further reduces the overall longitudinal length of the filter.

In this case the filter body 102 is fixed directly to the filter support at the inlet end 104 by wrapping two flaps 900 of the filter body 102 around the support wires 116 and then fixing the flaps 900 to the filter body 102 in this wrapped position.

Figure 27:
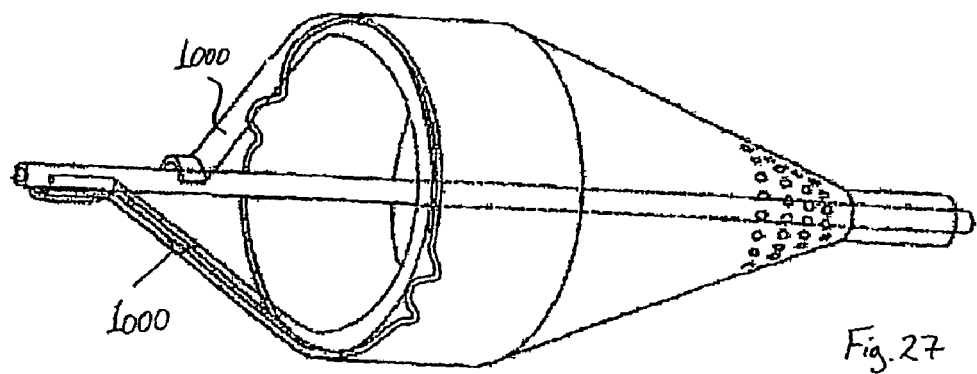

The filter of FIG. 27 has two proximal support legs 1000 which are axially offset.

Figure 29:
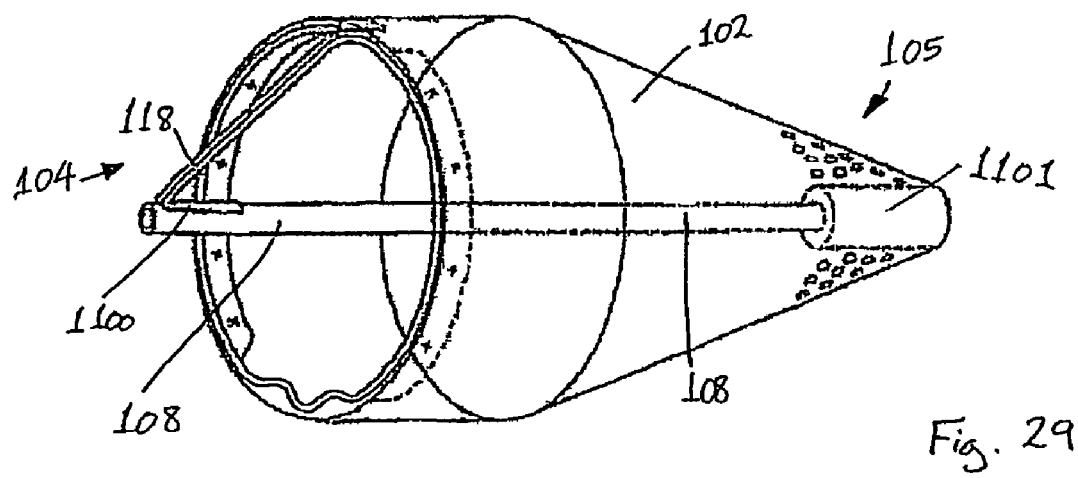

In the filter element of FIG. 29, the support leg 118 is fixed to the inner tube 108 at an inner foot section 1100. The inner section 1100 is inverted to extend distally along the inner tube 108. In addition, the filter body 102 is configured to slide distally over the inner tube 108 upon collapse by means of a sleeve 1101 fixed to the filter body 102 at the distal end 105. The sleeve 1101 is also inverted to extend proximally along the inner tube 108.

In this way, by inverting the inner section 1100 of the leg 118 and the sleeve 1101, the overall longitudinal length of the filter support is minimised. This results in less "parking space" in a vasculature being required to deploy the filter.

Furthermore, by extending the inner section 1100 of the leg 118 distally, the possibility of embolic material becoming caught or hung-up at the inlet end 104 of the filter element is reduced.

Figure 30:
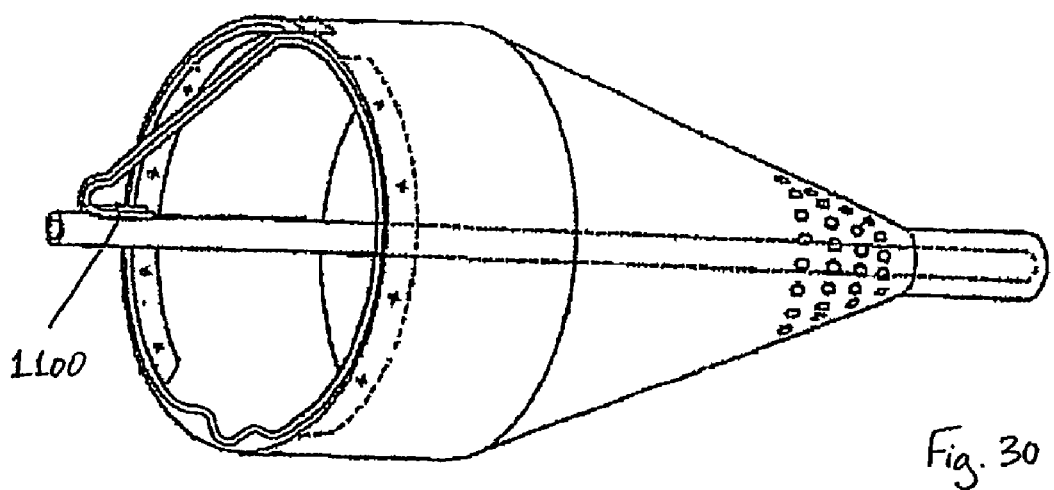

Referring to FIG. 30 another filter which has a more enhanced transition to the foot 1100 is illustrated.

Figure 28:
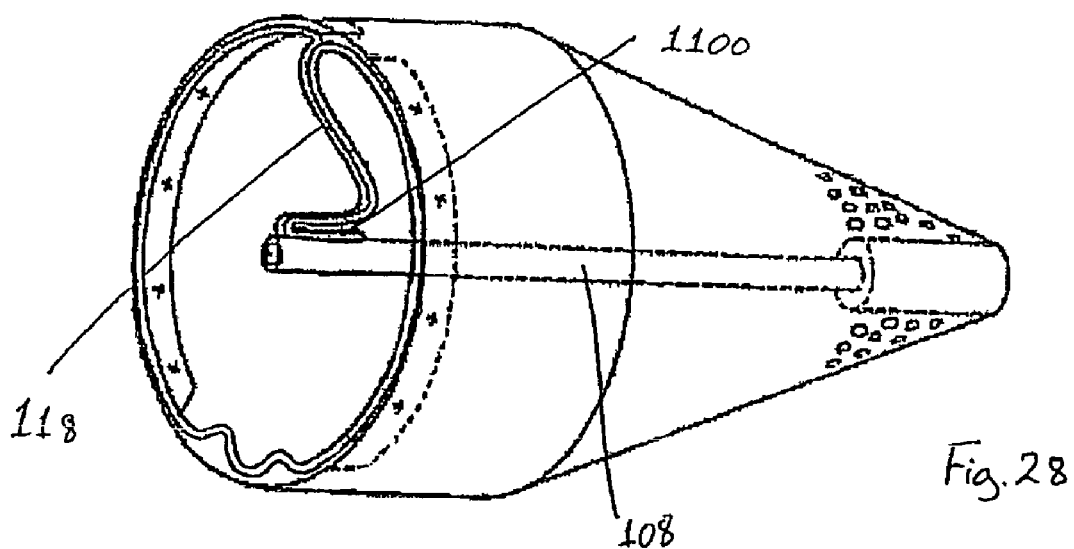

The filter of FIG. 28 has a proximal support leg 118 that extends distally to minimise the length and hence the parking space of the filter. A support foot 1100 is again provided for load distribution.

Figures 31, 32:
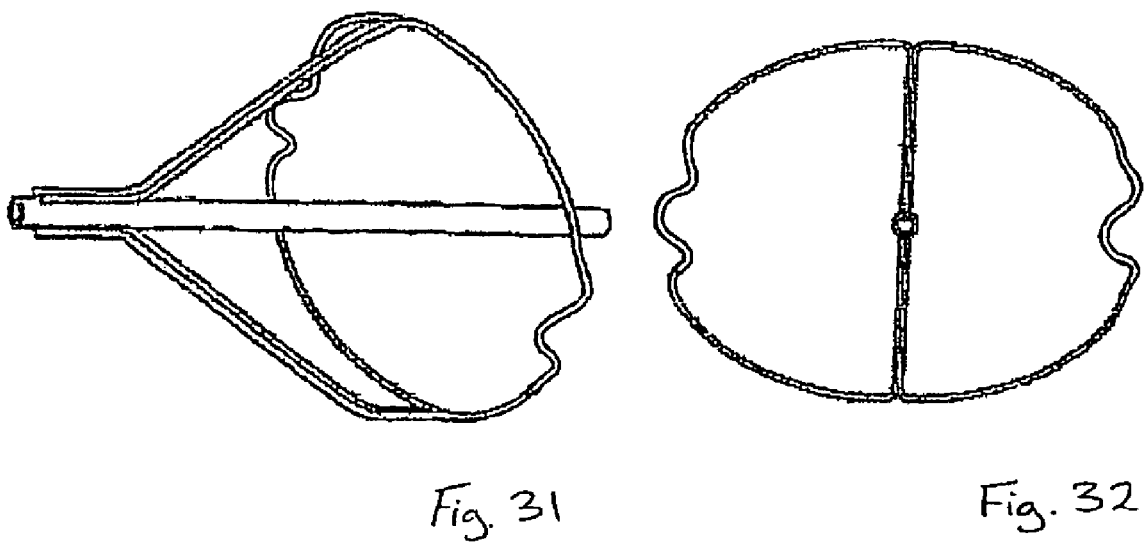
Figure 33:
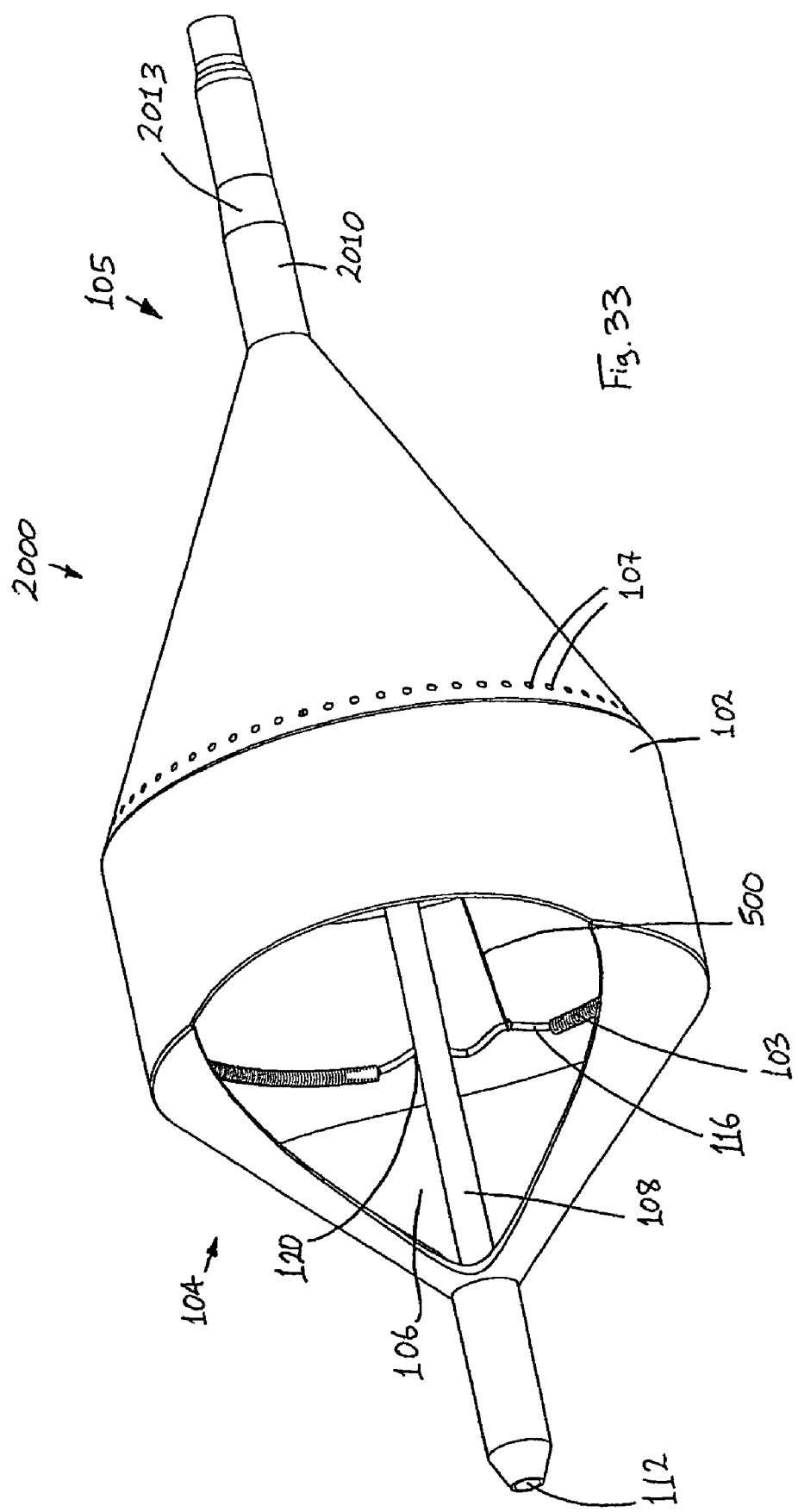
FIG. 33 is a perspective view of another embolic protection device according to the invention.
Figure 34:
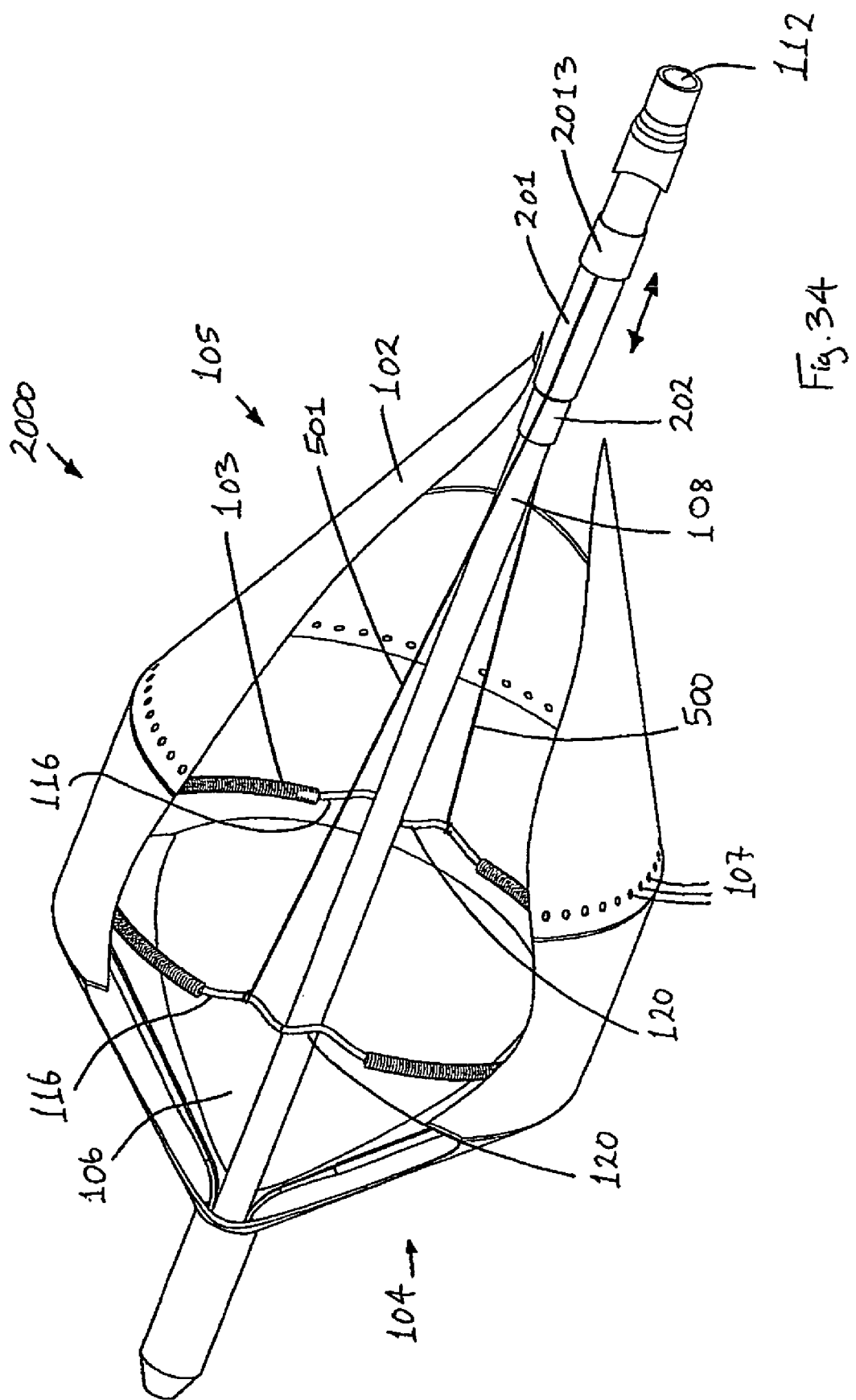
FIG. 34 is a partially cut-away, perspective view of the device of FIG. 33.

Various alternative support frames are possible. In the support frames of FIGS. 31 and 32 the hoop is biased towards an elliptical shape in its unconstrained state. When constrained within a vessel the major axis of the elipse will be compressed, which will tend to expand the minor axis. This action may assist in the even distribution of radial force to the vessel wall in the case where the support frame is inherently more flexible at the loops than at the top of its proximal arms.

Referring to FIGS. 33 to 39 there is illustrated another embolic protection device 2000 according to the invention, which is similar to the device 200 of FIGS. 12 to 19, and similar elements in FIGS. 35 to 39 are assigned the same reference numerals.

Figure 35:
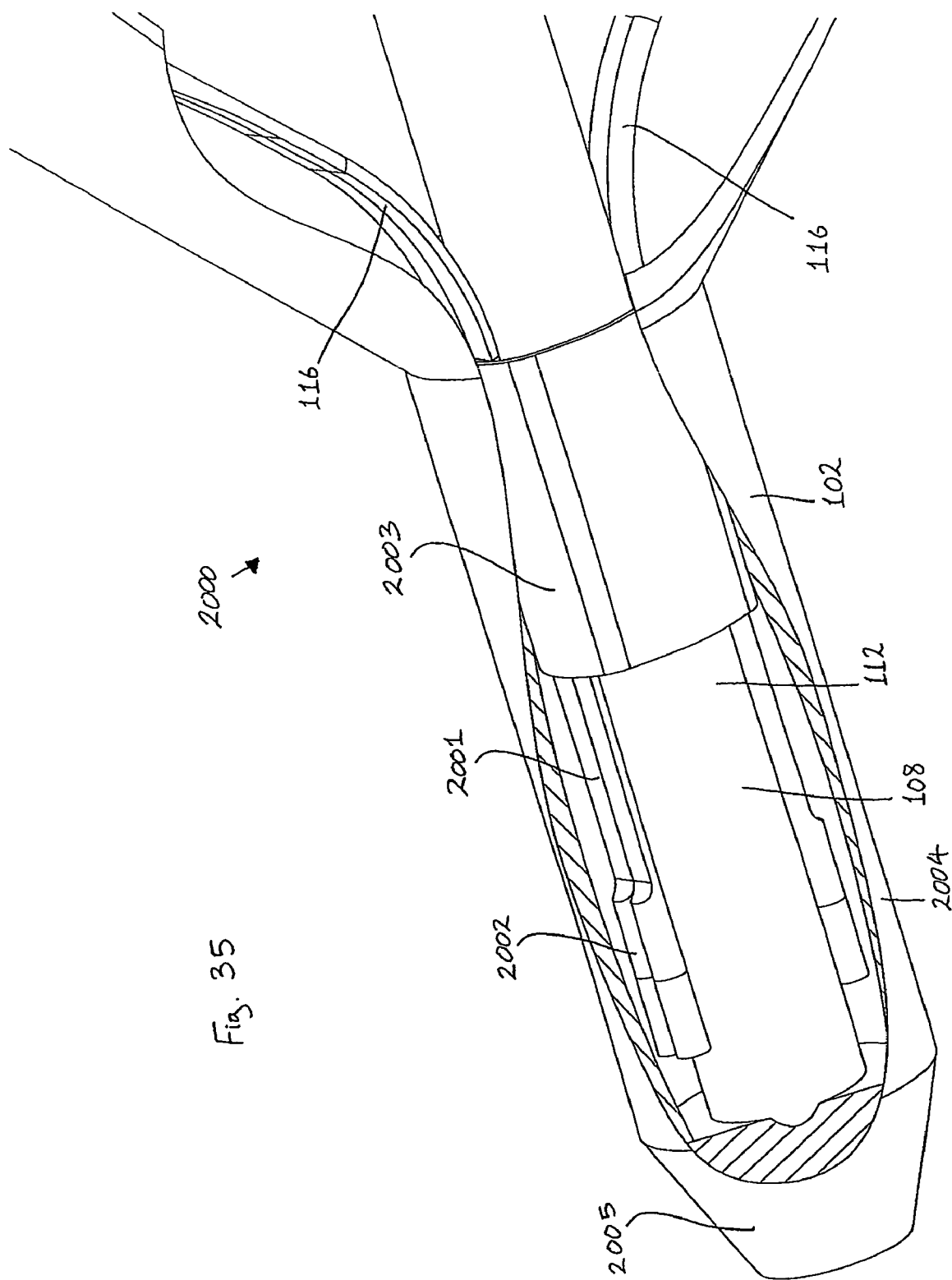
FIG. 35 is a cut-away, perspective view of a proximal end of the device of FIG. 33.

In this case each proximal leg 118 has a flattened portion 2001 and an unflattened, rounded portion 2002 proximally of the marker band 2003 (FIG. 35). The rounded portion 2002 may act as a stop. The proximal neck 2004 of the filter body 102 is bonded to the marker band 2003, to the support frame legs 118 and to the filter carrier 108.

An adhesive fillet 2005 is located proximally of the rounded portion 2002.

Figure 36:
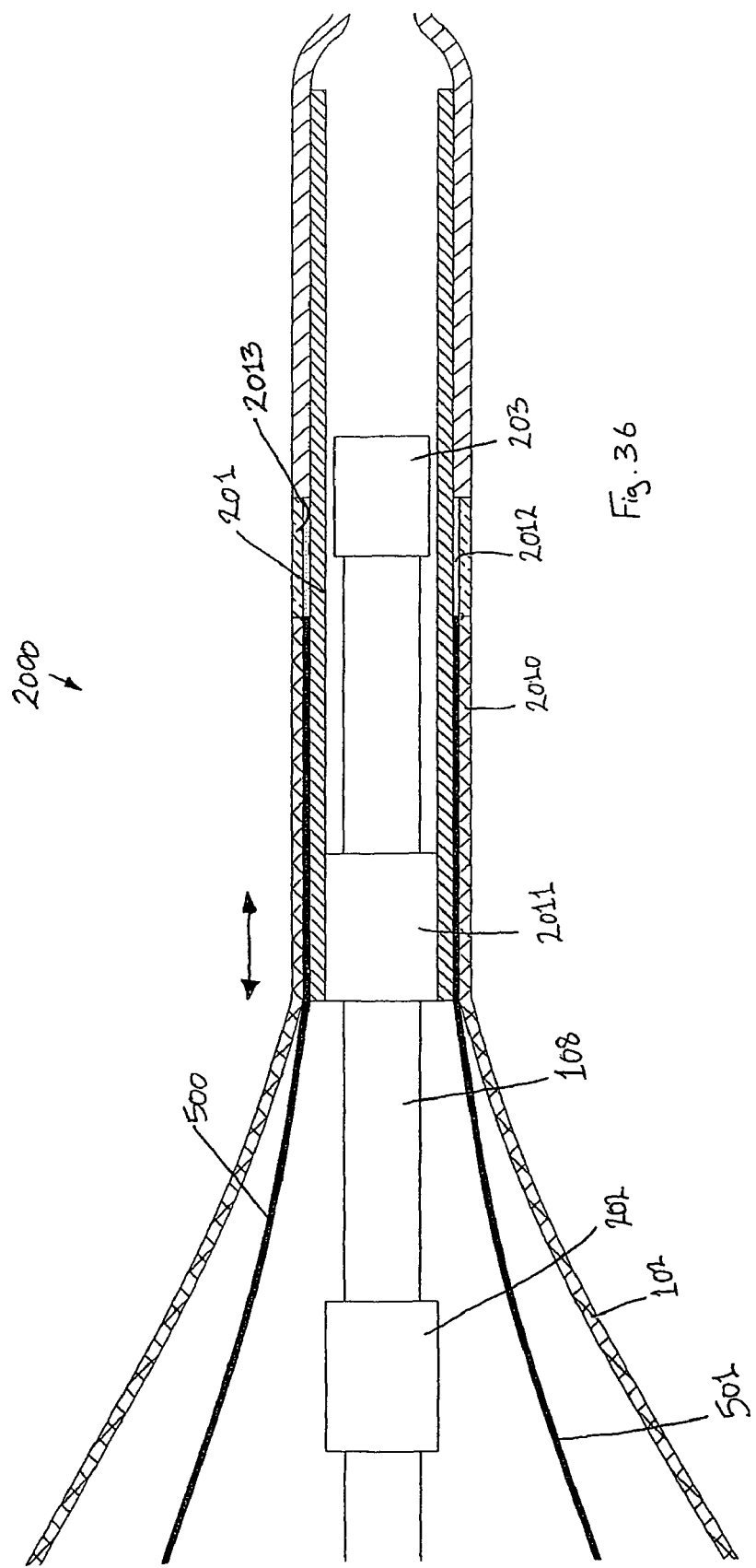
FIG. 36 is a cross-sectional, side view of a distal end of the device of FIG. 33.
Figure 37:
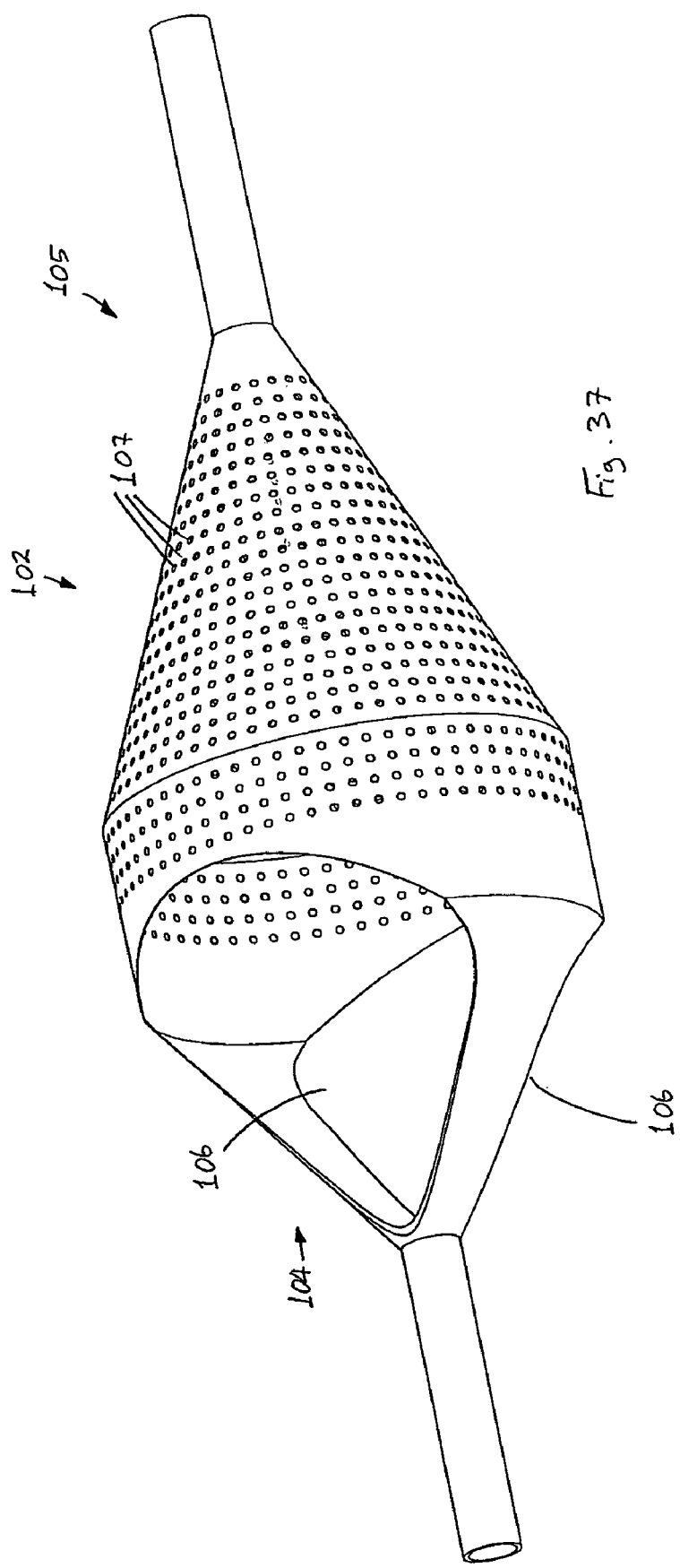
FIG. 37 is a perspective view of a filter body of the device of FIG. 33.
Figure 38:
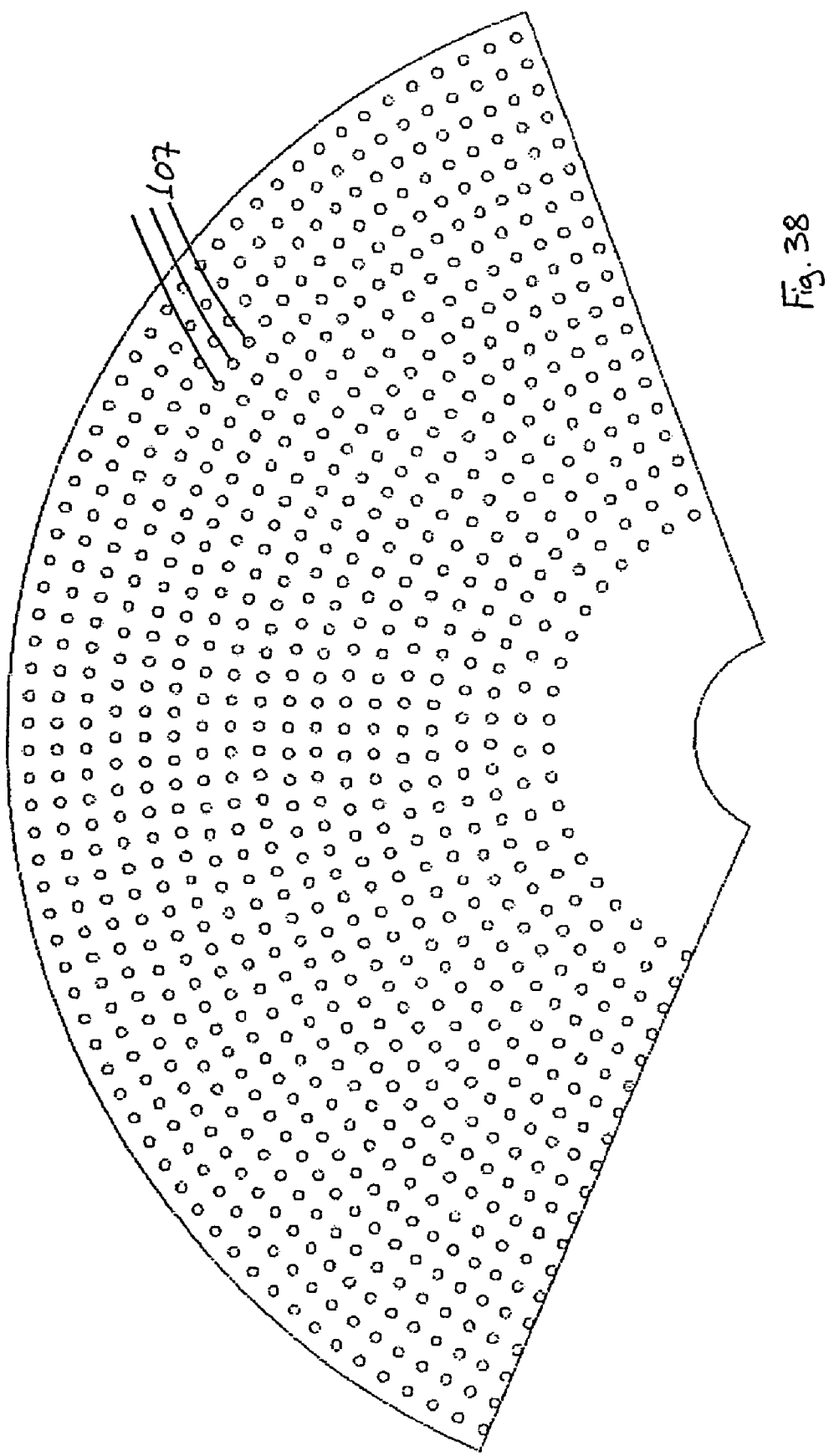
FIG. 38 is a development view of a part of the filter body of FIG. 37.
Figure 39:
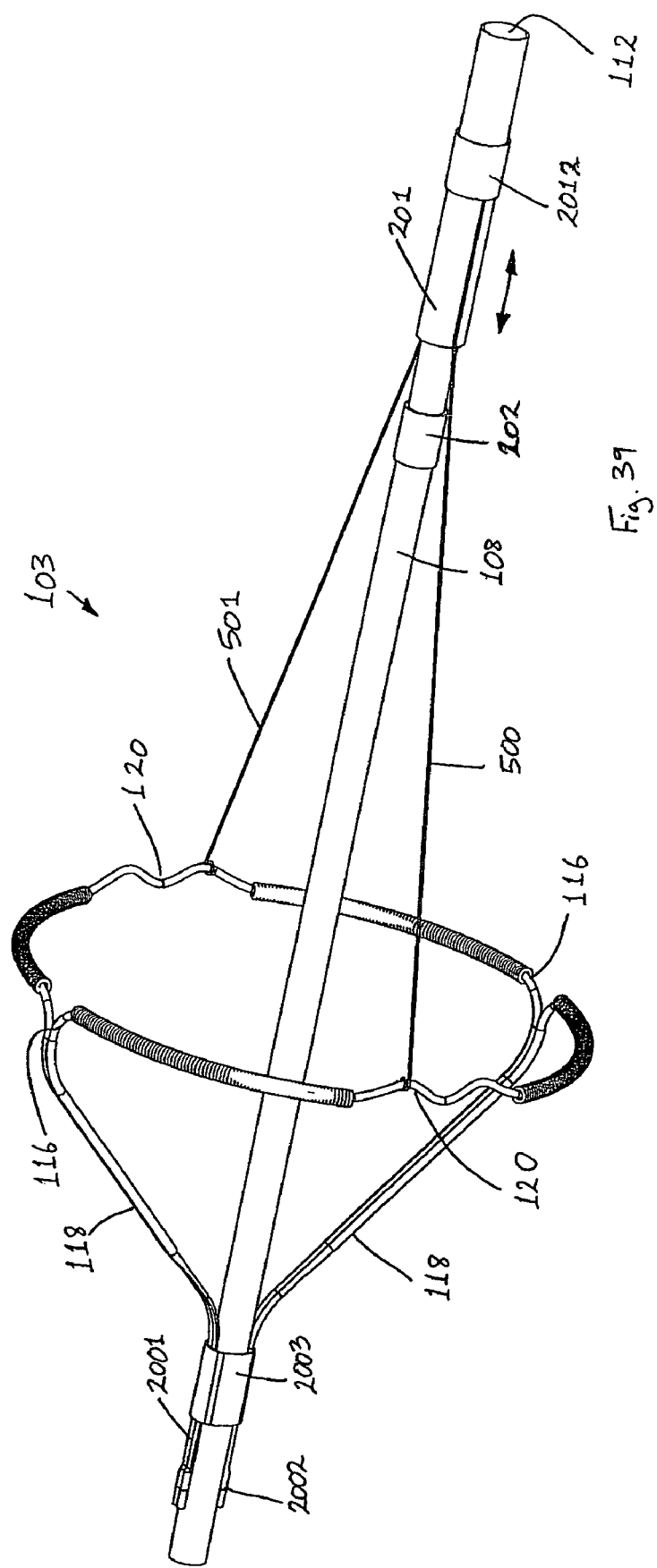
FIG. 39 is a perspective view of a filter support and a carrier of the device of FIG. 33.

Each tether 500, 501 is fixedly attached to the sleeve 201 and to the distal olive portion 2010 of the filter body 102 (FIG. 36). The sleeve 201 is attached to a slider 2011 which is slidably movable over the filter carrier 108 between the proximal stop 202 and the distal stop 203.

A marker band 2012 and an adhesive fillet 2013 are fixedly attached to the distal portion 2010 of the filter body 102.

The stops 202, 203 are fixedly attached to the filter carrier 108.

Figure 40:
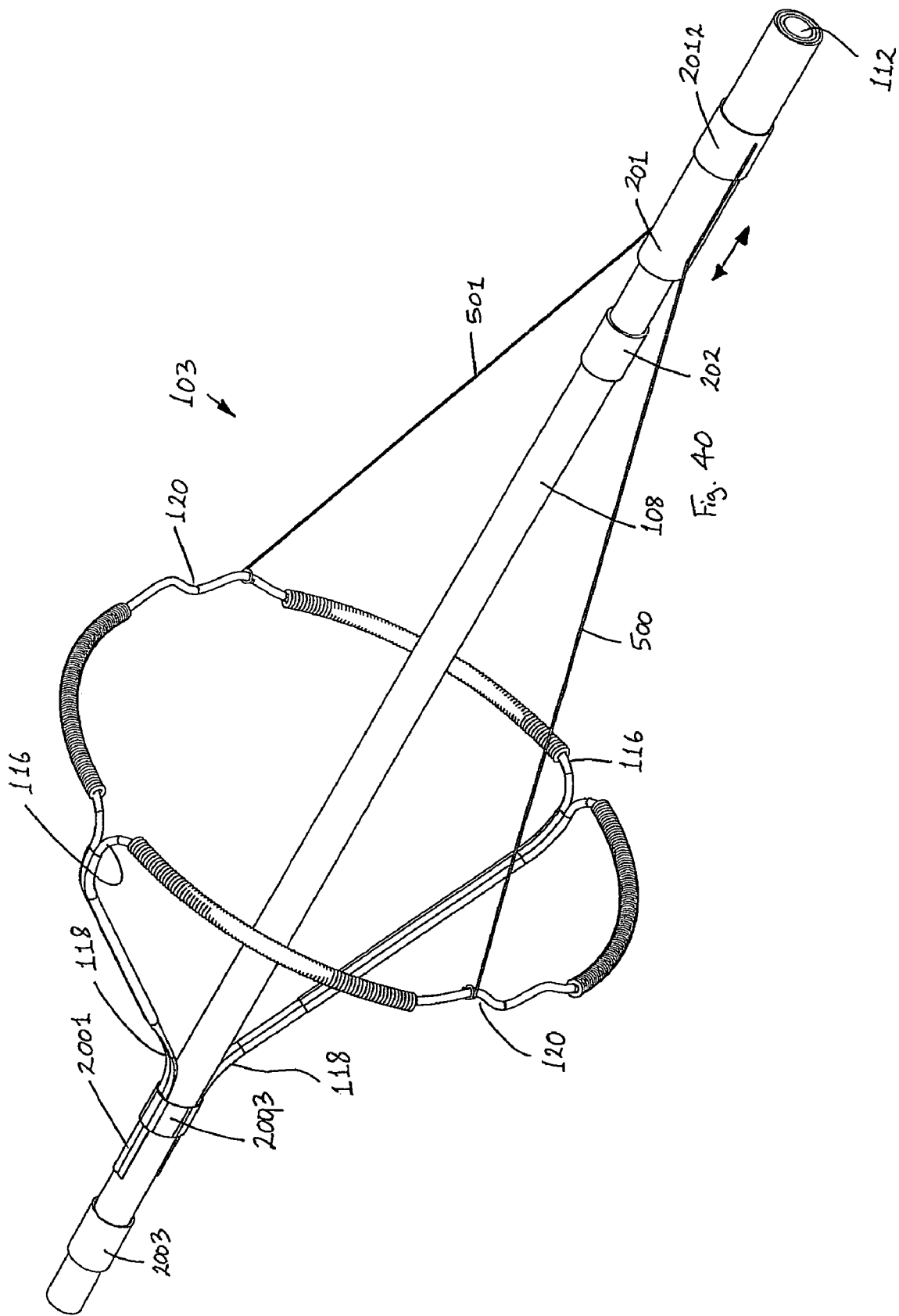
FIG. 40 is a perspective view of a filter support and a carrier of another embolic protection device according to the invention.

FIG. 40 illustrates an alternative embodiment. In this case each proximal leg 118 is flattened for the full length of the portion 2001 proximally of a coupling sleeve 2093. The marker band 2003 is located proximally of the flattened portion 2001.

Figure 41:
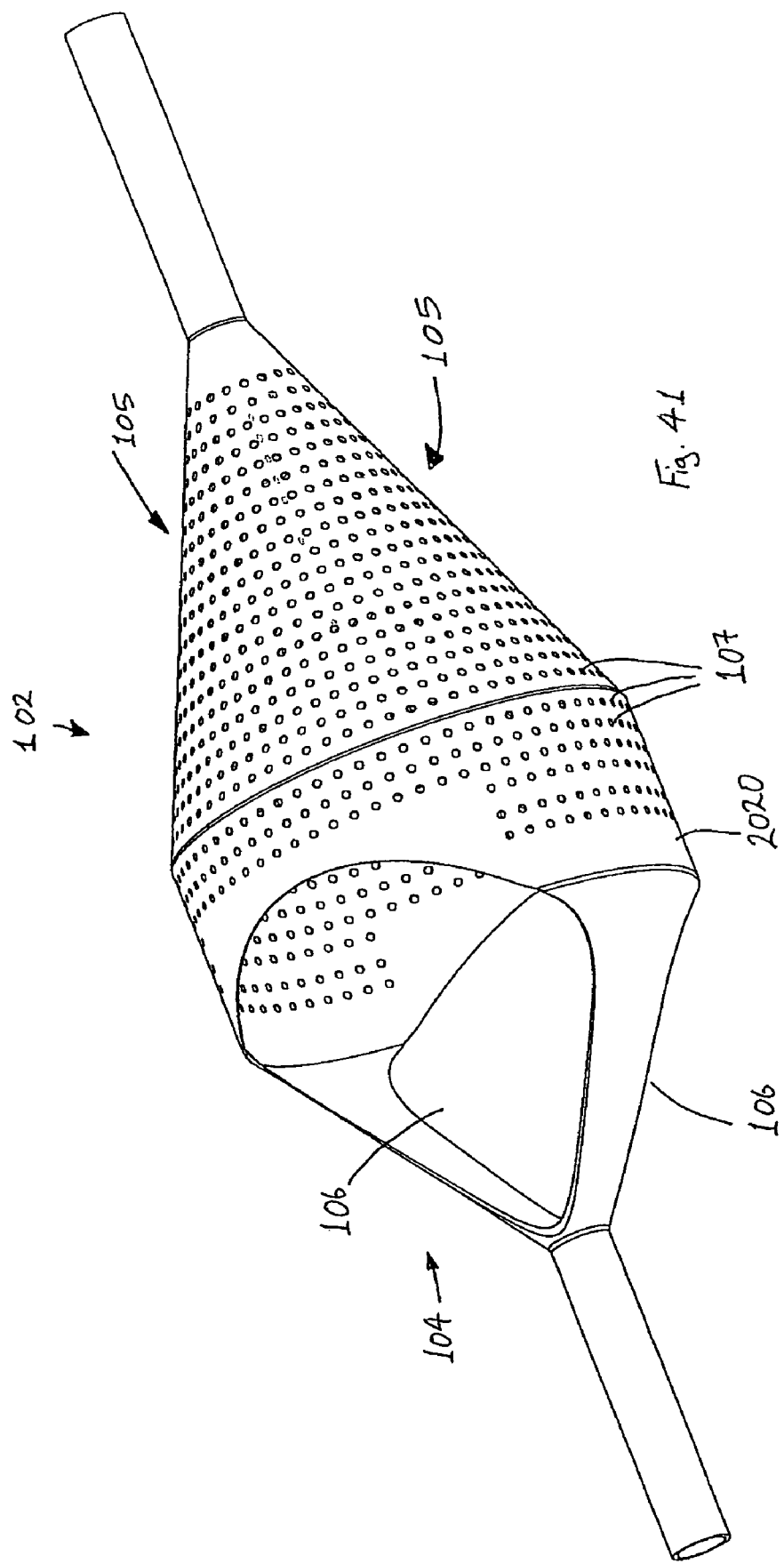
FIG. 41 is a perspective view of a filter body of another embolic protection device according to the invention.

The hole pattern across the filter body 102 may be varied to suit requirements. For example in the embodiment of FIG. 41, the outlet openings 107 are provided at the outlet end 105 of the filter body 102 and also along the intermediate portion 2020.

Figure 42:
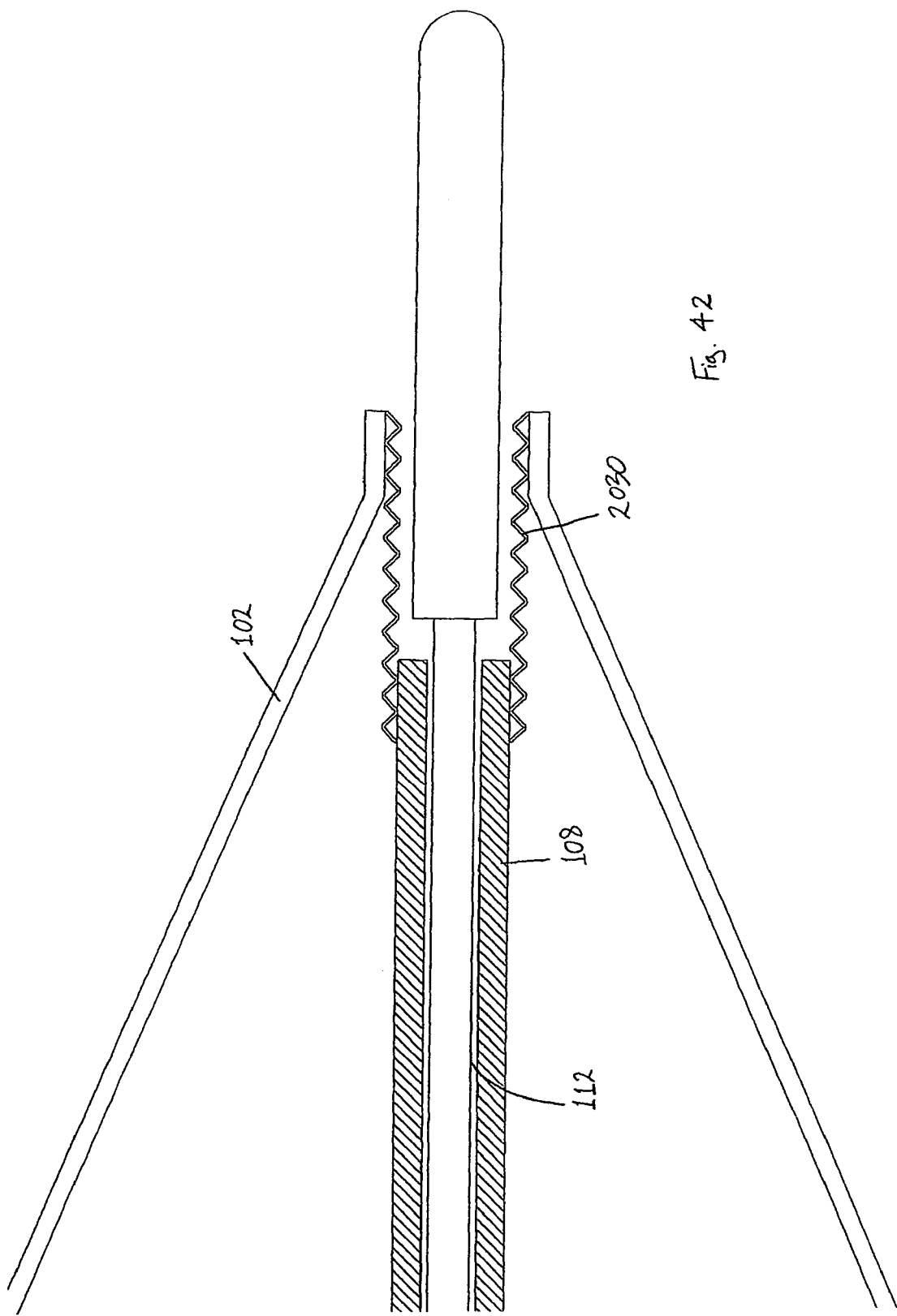
Figure 43:
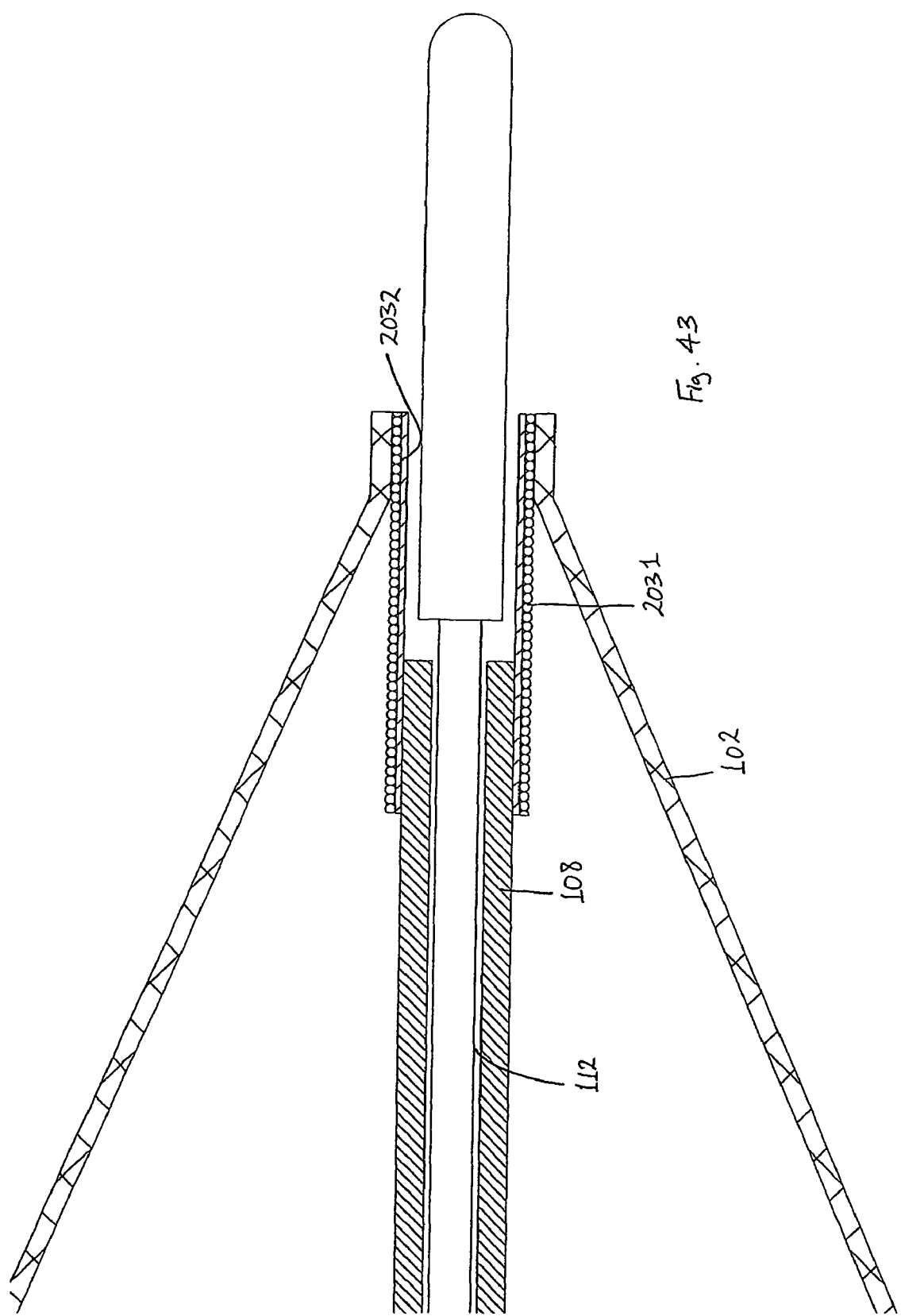
Figure 44:
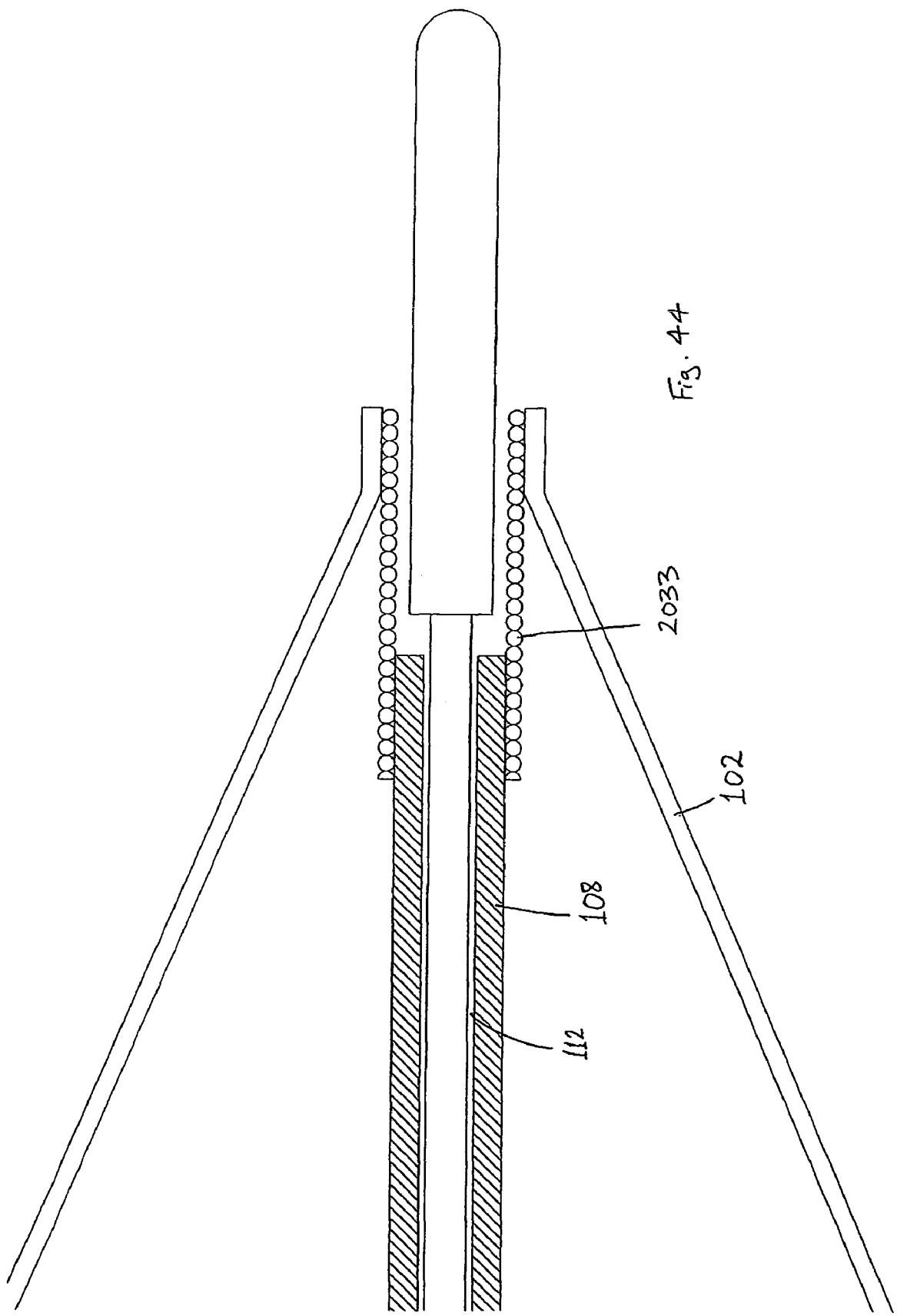

It will be appreciated that the filter body 102 may be coupled to the filter carrier 108 in a sliding manner in a number of different configurations. For example as an alternative to the sliding sleeve 201 and the stops 202, 203, the filter body 102 may be attached to the filter carrier 108 by a stretchable concertina member 2030 (FIG. 42), and/or by a spring member 2031 and an expansile polymer member 2032 (FIG. 43), and/or by a spring member 2033 only (FIG. 44), and/or by an expansile polymer member 2034 only (FIG. 45).

The expansile polymer 2032 may be over-moulded onto the spring 2031 or the expansile polymer 2032 may be heat shrunk onto the spring 2031. The expansile polymer 2032 may contain PTFE filler to impart low friction properties.

The invention is not limited to the embodiments hereinbefore described, with reference to the accompanying drawings, which may be varied in construction and detail.

The invention claimed is:

1. An embolic protection device comprising:
a collapsible filter element for delivery through a vascular system of a patient;
the filter element comprising a collapsible filter body and a filter support for the filter body;
the filter body having an inlet end and an outlet end, the inlet end of the filter body having one or more inlet openings sized to allow blood and embolic material enter the filter body, the outlet end of the filter body having a plurality of outlet opening sized to allow through passage of blood but to retain undesired embolic material within the filter body;
the filter support being movable between a collapsed configuration and an extended outwardly projecting deployed configuration to support the filter body in an expanded configuration;
the filter support comprising a plurality of segments, at least some of the segments being interconnected by a strain distributing linking element;
in the collapsed configuration, the strain distributing linking element defining a low-profile relative to a cylindrical shaped filter carrier,
wherein the strain distributing linking element has a concave portion and, in the collapsed configuration, the concave portion faces radially inwardly to wrap around a part of the filter carrier.

2. A device as claimed in claim 1 wherein in the collapsed configuration, the strain distributing linking element extends circumferentially around at least part of the carrier.

3. A device as claimed in claim 1 wherein the radius of curvature of the concave portion of the curve is approximately equal to an external radius of the carrier.

4. A device as claimed in claim 1 wherein in the extended outwardly projecting configuration, the concave portion of the curve faces longitudinally.

5. A device as claimed in claim 1 wherein in the extended outwardly projecting configuration, the concave portion of the curve faces distally.

6. A device as claimed in claim 1 wherein the filter support comprises a first segment and a second segment, the first segment being located adjacent to the second segment and being connected to the second segment by the strain distributing linking element, in the extended outwardly projecting configuration, the axis of the first segment being substantially aligned with the axis of the second segment.

7. A device as claimed in claim 6 wherein in the extended outwardly projecting configuration, the aligned axes of the first and second segments intersect the concave portion of the curve.

8. A device as claimed in claim 7 wherein in the extended outwardly projecting configuration, the inner part of the concave portion of the curve is located to one side of the aligned axes of the first and second segments, and the outer ends of the concave portion of the curve are located to an opposite side of the aligned axes of the first and second segments.

9. A device as claimed in claim 8 wherein in the extended outwardly projecting configuration, the inner part of the concave portion of the curve is located proximally of the aligned axes of the first and second segments, and the outer ends of the concave portion of the curve are located distally of the aligned axes of the first and second segments.

10. A device as claimed in claim 6 wherein in the collapsed configuration, the axis of the first segment is out of alignment with the axis of the second segment.

11. A device as claimed in claim 10 wherein the strain distributing linking element undergoes a shape change from a first shape in the extended outwardly projecting configuration to a second shape in the collapsed configuration to accommodate the change in alignment of the first and second segments.

12. A device as claimed in claim 10 wherein the strain distributing linking element undergoes a rotation from the extended outwardly projecting configuration to the collapsed configuration to accommodate the change in alignment of the first and second segments.

13. A device as claimed in claim 6 wherein in the extended outwardly projecting configuration, the strain distributing linking element defines a first plane and the segments define a second plane substantially perpendicular to the first plane.

14. A device as claimed in claim 1 wherein the strain distributing linking element has a substantially sine-wave shape.

15. A device as claimed in claim 1 wherein each segment has a termination, and the terminations of adjacent segments are fixedly attached to one another along the length of the terminations, and extend generally parallel.

16. A device as claimed in claim 15 wherein the filter support comprises a fixing element extending along at least part of the terminations to fixedly attach the terminations to one another.

17. A device as claimed in claim 16 wherein the fixing element comprises a sleeve extending along at least part of the terminations.

18. A device as claimed in claim 15 wherein the terminations extend generally axially.

19. A device as claimed in claim 1 wherein the filter element comprises the carrier.

20. A device as claimed in claim 19 wherein a proximal end of the carrier is located proximally of the inlet end of the filter body.

21. A device as claimed in claim 19 wherein a distal end of the carrier is located distally of the outlet end of the filter body.

22. A device as claimed in claim 19 wherein the carrier is provided separate from the filter support.

23. A device as claimed in claim 19 wherein the carrier is movable relative to a guidewire.

24. A device as claimed in claim 23 wherein the carrier is slidable relative to a guidewire.

25. A device as claimed in claim 23 wherein the carrier is rotatable relative to a guidewire.

26. A device as claimed in claim 19 wherein the carrier comprises a guidewire.

27. A device as claimed in claim 1, wherein the concave portion of the strain distributing linking element is between two convex portions, and in the extended position, the concave portion and both convex portions face longitudinally in the distal direction.

28. A device as claimed in claim 27, wherein the carrier is a tubular sleeve, and the radius of curvature of the concave portion is approximately equal to the external radius of the carrier.

29. A device as claimed in claim 28, wherein the concave portion extends circumferentially around approximately 180 degrees of the circumference of the tubular sleeve.

30. An embolic protection device comprising:
a collapsible filter element for delivery through a vascular system of a patient;
the filter element comprising a collapsible filter body and a filter support for the filter body;
the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
the filter support being movable between a collapsed configuration for movement through the vascular system, and an extended outwardly projecting deployed configuration to support the filter body in an expanded configuration;
the filter support comprising a plurality of segments, at least some of the segments being interconnected by a strain distributing linking element; and
the strain distributing linking element being at least partially curved, in the extended outwardly projecting configuration the strain distributing linking element comprising a first convex portion, a second convex portion adjacent to the first convex portion and a concave portion between the convex portions,
wherein in the collapsed configuration, the concave portion faces radially inwardly to wrap around a part of a filter carrier.

31. A device as claimed in claim 30 wherein in the extended outwardly projecting configuration, the convex portions face longitudinally.

32. A device as claimed in claim 31 wherein in the extended outwardly projecting configuration, the convex portions face distally.

33. A device as claimed in claim 30 wherein in the extended outwardly projecting configuration, the concave portion faces longitudinally.

34. A device as claimed in claim 30 wherein in the extended outwardly projecting configuration, the concave portion faces distally.

35. A device as claimed in claim 30, wherein the concave portion extends circumferentially around approximately 180 degrees of the circumference of the carrier.

36. A device as claimed in claim 30, wherein the radius of curvature of the concave portion of the curve is approximately equal to an external radius of the carrier.

37. An embolic protection device comprising:
a collapsible filter element for delivery through a vascular system of a patient;
the filter element comprising a collapsible filter body and a filter support for the filter body;
the filter body having an inlet end and an outlet end, the inlet end of the filter body having one or more inlet openings sized to allow blood and embolic material enter the filter body, the outlet end of the filter body having a plurality of outlet openings sized to allow through passage of blood but to retain undesired embolic material within the filter body;
the filter support being movable between a collapsed configuration for movement through the vascular system, and an extended outwardly projecting deployed configuration to support the filter body in an expanded configuration;
the filter support comprising a plurality of segments, at least some of the segments being interconnected by a strain distributing linking element, and a radiopaque element along at least part of at least one segment,
wherein the strain distributing linking has a concave portion and, in the collapsed configuration, the concave portion faces radially inwardly to wrap around a part of a filter carrier.

38. A device as claimed in claim 37, wherein the concave portion of the strain distributing linking element is between two convex portions, and in the extended position, the concave portion and both convex portions face longitudinally in the distal direction.

39. An embolic protection device comprising:
a collapsible filter element for delivery through a vascular system of a patient;
the filter element comprising a collapsible filter body and a filter support for the filter body;
the filter body having an inlet and an outlet end, the inlet end of the filter body having one or more inlet openings sized to allow blood and embolic material enter the body, the outlet end of the filter body having a plurality of outlet openings sized to allow through passage of blood but to retain undesired embolic material within the filter body;
the filter support being movable between a collapsed configuration for movement through the vascular system, and an extended outwardly projecting deployed configuration to support the filter body in an expanded configuration;
the filter element comprising a plurality of segments, at least some of the segments being interconnected by two strain distributing linking elements;
in the collapsed configuration, the two strain distributing linking elements being longitudinally offset, wherein the strain distributing linking elements have a concave portion and, in the collapsed configuration, the concave portions faces radially inwardly to wrap around a part of a filter carrier.

40. A device as claimed in claim 39, wherein each concave portion of the strain distributing linking elements is between two convex portions, and in the extended position, the concave portions and convex portions face longitudinally in the distal direction.

* * * * *